United States Patent
Rivet et al.

(10) Patent No.: US 10,253,287 B2
(45) Date of Patent: Apr. 9, 2019

(54) IN VITRO CULTURE MODEL OF ANISOTROPIC TO ISOTROPIC TRANSITIONS

(71) Applicant: RENSSELAER POLYTECHNIC INSTITUTE, Troy, NY (US)

(72) Inventors: Christopher John Rivet, Grand Blanc, MI (US); Gregory Patrick Desmond, Marshfield, MA (US); Jonathan Michael Zuidema, Grand Haven, MI (US); Ryan James Gilbert, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 15/506,974

(22) PCT Filed: Aug. 25, 2015

(86) PCT No.: PCT/US2015/046664
§ 371 (c)(1),
(2) Date: Feb. 27, 2017

(87) PCT Pub. No.: WO2016/033022
PCT Pub. Date: Mar. 3, 2016

(65) Prior Publication Data
US 2017/0253843 A1    Sep. 7, 2017

Related U.S. Application Data

(60) Provisional application No. 62/041,261, filed on Aug. 25, 2014.

(51) Int. Cl.
| | | |
|---|---|---|
| *C12M 3/00* | (2006.01) |
| *C12M 1/00* | (2006.01) |
| *C12M 1/12* | (2006.01) |
| *C12N 5/00* | (2006.01) |
| *C12N 5/079* | (2010.01) |

(52) U.S. Cl.
CPC ............ *C12M 21/08* (2013.01); *C12M 23/20* (2013.01); *C12M 25/14* (2013.01); *C12N 5/0068* (2013.01); *C12N 5/0622* (2013.01)

(58) Field of Classification Search
None
See application file for complete search history.

(56) References Cited

U.S. PATENT DOCUMENTS

2010/0331980 A1    12/2010    Lee et al.

FOREIGN PATENT DOCUMENTS

| JP | 2002249966 A | 9/2002 | |
|---|---|---|---|
| JP | 2013520168 A | 6/2013 | |
| WO | WO-2007121353 A1 * | 10/2007 | ............ B82Y 30/00 |
| WO | WO-2011123798 A2 | 4/2011 | |

OTHER PUBLICATIONS

Tsuruma et al. Colloids and Surfaces A: Physiochem. Eng. Aspects (2006) 284-285: 470-474 (Year: 2006).*
International Search Report in International Application No. PCT/US2015/046664, filed Aug. 25, 2015.
Wang, Han Bing, et al, Creation of highly aligned electrospun poly-L-lactic acid fibers for nerve regeneration applications, Journal of Neural Engineering, 2009, pp. 1-15, 6, 016001, iopscience.iop.org, IOP Publishing Ltd, UK.
Zuidema, Jonathan M., et al, Nebulized solvent ablation of aligned PLLA fibers for the study of neurite response to anisotropic-to-isoptropic fiber/film transition (AFFT) boundaries in astrocyte-neuron co-cultures, Biomaterials, 2015, 46, pp. 82-94, www.elsevier.com/locate/biomaterials, Elsevier Ltd.

* cited by examiner

*Primary Examiner* — Susan M Hanley
(74) *Attorney, Agent, or Firm* — Murtha Cullina LLP; Anthony P. Gangemi

(57) ABSTRACT

Cell culture devices, and related methods and kits, for modeling isotropic-to-anisotropic cellular transitions are provided. The devices can include a substrate having an isotropic film surface with one or more regions of aligned fibers dispersed thereon.

13 Claims, 24 Drawing Sheets

| Neurite Growth Into Gap | | % Of Total Neurites |
|---|---|---|
| 0 | | 25 |
| 0-50 | | 39 |
| 50-100 | | 22 |
| 100-150 | | 7 |
| 150-200 | | 7 |

IN VITRO CULTURE MODEL OF ANISOTROPIC TO ISOTROPIC TRANSITIONS

CROSS-REFERENCE TO RELATED APPLICATIONS

This application is the U.S. national stage application of International Patent Application No. PCT/US2015/046664, filed Aug. 25, 2015, which claims the benefit of U.S. Provisional Application Ser. No. 62/041,261, filed Aug. 25, 2014, which is incorporated herein by reference in its entirety.

GOVERNMENT SUPPORT

This invention was made with government support under National Science Foundation grant NSF CAREER Award 1105125 and NSF I-Corps Grant IIP-1358895 to RJG, and NIH RO1 1RO1EB013281 to DMT. The government has certain rights in the invention.

BACKGROUND OF THE INVENTION

Greater understanding of the cellular changes in response to biomaterial topography has allowed for biomaterials to be developed that specifically alter cellular behavior to elicit more efficient tissue regeneration (Anselme et al., 2010; Hoffman-Kim et al., 2010; Lim and Donahue, 2007). Several different modalities of biomaterials are used to examine glial or neuronal responses to micro- and nano-surface topographies. For example, astroglial cells attach more strongly to microfabricated pillars rather than to smooth substrates (Turner et al., 2000). Polymer microchannels have been shown to induce hippocampal neuron polarization more so than immobilized nerve growth factor on smooth substrates (Gomez et al., 2007). Neural cell lines cultured on polymer nanowires induced these neurons to produce more neural markers in comparison to the neural cells cultured on smooth surfaces (Bechara et al., 2010).

Aligned, electrospun fibers, another type of biomaterial topography, directed the extension of neurites and helped mature Schwann cell differentiation (Corey et al., 2007; Wang et al., 2009; Chew et al., 2008). Deciphering the mechanisms by which topography influences glial or neuronal behavior in manners supportive of regeneration will lead to better biomaterial strategies to repair the injured nervous system.

Of the topographical biomaterials stated above, aligned, electrospun fibers are most commonly used to mimic the anisotropic structural assembly of axons and glia in the uninjured peripheral nervous system (Bellamkonda, 2006) and within the white matter tracts of the uninjured spinal cord (Silver and Miller, 2004). The ability of aligned, electrospun fiber topography to direct regeneration and recreate the anisotropic structure within the peripheral nerve or spinal cord is communicated clearly within recent in vivo studies (Chew et al., 2007; Kim et al., 2008; Gelain et al., 2011; Hurtado et al., 2011; Liu et al., 2012). In experimental models of spinal cord injury specifically, electrospun fiber topography was able to encourage a subset of astrocytes to migrate into an electrospun fiber-containing conduit instead of forming an astroglial scar (Hurtado et al., 2011). These studies demonstrate that electrospun fibers have the potential to not only direct axonal regeneration, but also to direct the migration of astrocytes supportive of axonal regeneration.

While it is established that aligned, electrospun topography has the ability to direct axonal regeneration within experimental models of spinal cord injury, aligned fibers also may be utilized to develop in vitro models able to recapitulate transitions from healthy tissue to injured tissue. Studies involving topographical biomaterial constructs present cells with uniform topography, and cellular responses to such topography are compared to separate cultures where cells are cultured on flat surface controls (Hurtado et al., 2011; Koppes et al., 2014).

One injury with an anisotropic-to-isotropic transition is spinal cord injury (SCI), specifically within the white matter tracts. Following SCI, the extracellular environment is drastically altered, leading to changes in the composition and organization of the extracellular matrix. Furthermore, the distribution and alignment of astrocytes at the lesion edge becomes disorganized (Silver and Miller, 2004; Wanner et al., 2013). Immediately following injury, astrocytes migrate to the lesion edge, become hypertrophic and elongated, and create a dense cellular construct (termed the glial scar) (Silver and Miller, 2004; Wanner et al., 2013). These reactive astrocytes at the lesion edge alter the extracellular environment by up-regulating axonal extension-inhibiting chondroitin sulfate proteoglycans (CSPGs) (Silver and Miller, 2004; Liu et al., 2012). Spared and regenerating axons within the white matter tract then extend to the lesion edge, where they become dystrophic (Tom et al., 2004) and are not likely to cross into the lesion site due to the presence of axonal inhibitors (Sharma et al., 2012; Pernet and Schwab, 2012) and the lack of a bridging scaffold to direct axonal regeneration (Cheng et al., 1996).

Changes in extracellular composition and cellular function are very dynamic following SCI. While in vivo rodent models can provide information representative of spinal cord injury within humans (Cheriyan et al., 2014), the surgeries require exceptional expertise. Additionally, the studies are very time consuming.

BRIEF SUMMARY OF THE INVENTION

There are currently no available biomaterial constructs that possess both aligned, electrospun fiber topography and non-topographical features within the same construct. The present invention addresses this need and provides cell culture devices, and related kits and methods, for modeling isotropic-to-anisotropic cellular transitions that are observed in injured tissues, such as for example, spinal cord injury, tendon injury, and muscle injury. Such constructs provide information on how cells behave on topographical to non-topographical interfaces within the same culture, or to create models that mimic injury environments where cells at the lesion interface are not provided with topographical cues. Biomaterial constructs possessing topographical and non-topographical domains with a subset of cells, such as cells found within the spinal cord, may be used to assess the efficacy of pharmacological agents or to understand changes in cellular physiology at anisotropic-to-isotropic transitions without great difficulty or expense of time.

In one aspect, the present invention provides a cell culture apparatus for modeling isotropic-to-anisotropic cellular transitions, comprising a substrate comprising an isotropic film surface with one or more regions of aligned fibers dispersed thereon. The aligned fibers and the isotropic film surface on the substrate provide a topographic-to-non-topographic transitional boundary therebetween. In some embodiments, the fibers are electrospun fibers. In some embodiments, the fibers and/or isotropic film surface comprise poly-L-lactic acid (PLLA).

In another aspect, the present invention provides methods of fabrication of a cell culture apparatus for modeling in vivo isotropic-to-anisotropic cellular transitions. The methods comprise depositing a collection film, such as, e.g., a PLLA film, onto a substrate; depositing fibers, such as, e.g., PLLA fibers, onto the collection film to form fiber scaffolds; and dissolving a subset of the fibers to yield one or more regions of an isotropic film surface that transition from the fiber scaffolds to form an anisotropic-to-isotropic fiber/film boundary. In some embodiments, the fibers are dissolved with chloroform, particularly nebulized chloroform, to yield an isotropic surface.

In another aspect, the present invention provides methods of modeling in vivo cellular response to isotropic-to-anisotropic topographic transitions in an in vitro model for tissue injury. The methods comprise providing a cell culture apparatus of the present invention, the apparatus comprising a substrate comprising an isotropic film surface with one or more regions of aligned fibers dispersed thereon; seeding one or more cells onto the substrate; allowing the cells to adhere to the one or more regions of aligned fibers; and allowing the cells to grow, whereby cell growth within the transitional boundary between the aligned fibers and the isotropic film surface models in vivo cell growth in isotropic-to-anisotropic topographic transitions of injured tissue. In some embodiments, the cells utilized in the methods provided herein are derived from neural tissue.

In yet another aspect, the present invention provides kits for examining cellular response to isotropic-to-anisotropic topographic transitions, comprising a cell culture apparatus of the present invention; and one or more reagent.

The devices, methods, and kits herein described can be used in connection with pharmaceutical, medical, and veterinary applications, as well as fundamental scientific research and methodologies, as would be identifiable by a skilled person upon reading of the present disclosure. These and other objects, features, and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures.

(FIG. 2A) SEM micrograph of aligned electrospun fibers. (FIG. 2B) Stereoscope image showing fiber-free gap within fiber scaffold. (FIGS. C-E) Graphs of the quantitative comparison of fiber diameter (FIG. 2C), fiber alignment (FIG. 2D), and fiber density (FIG. 2E) in control and AFFT scaffolds show no significant differences. Scale bars in FIG. 2A and FIG. 2B of 10 μm and 500 μm, respectively. Data in FIG. 2C and FIG. 2E are mean values±SE from five independently fabricated scaffolds.

(FIGS. 3A-C) 20× magnification images of a fluorescently-labeled fiber/AFFT scaffold (FIG. 3A), astrocytes cultured on the scaffold (FIG. 3B), and a merge of the two (FIG. 3C). (FIG. 3D) Quantification of astrocyte alignment at various locations within the scaffold. Scale bar=100 μm in FIG. 3C and can be applied to images FIG. 3A and FIG. 3B. Green signal represents GFAP in (FIG. 3C), while red signal is produced by rhodamine B within the fibers. Signal seen within the fiber-free gap appears due to leftover rhodamine following fiber dissolution. Data in (FIG. 3D) represent the mean values SE from four independently prepared cultures. * indicates statistical significance.

(FIGS. 4A-D) 20× magnification images of fluorescently-labeled fiber/AFFT scaffold (FIG. 4A), astrocytes cultured on scaffold (FIG. 4B), CSPGs produced by astrocytes (FIG. 4C), and a merge of the three (FIG. 4D). (FIG. 4E) Magnified image of aligned CSPGs from astrocytes on aligned scaffold region. (FIG. 4F) Magnified image of unaligned CSPGs from astrocytes within the AFFT. (FIG. 4G) Quantification of CSPG alignment at various locations within scaffold. Scale bar in FIG. 4D=100 μm and can be applied to FIG. 4A, FIG. 4B, and FIG. 4C. Scale bar in FIG. 4F=50 μm and can be applied to FIG. 4E. Green signal in FIG. 4D represents CSPGs, red signal represents GFAP, and blue signal represents rhodamine B within fibers. Data in FIG. 4G represent mean values±SE from four independently prepared cultures. * indicates statistical significance.

(FIGS. 5A-D) 20× magnification images of fluorescently-labeled fiber/AFFT scaffold (FIG. 5A), astrocytes cultured on scaffold (FIG. 5B), fibronectin from astrocytes (FIG. 5C), and a merge of the three (FIG. 5D). (FIG. 5E) Magnified image of aligned fibronectin produced by astrocytes on aligned scaffold region. (FIG. 5F) Magnified image of unaligned fibronectin produced by astrocytes within AFFT. (FIG. 5C) Quantification of CSPG alignment at various locations within scaffold. Scale bar in FIG. 5D=100 μm and can be applied to FIG. 5A, FIG. 5B, and FIG. 5C. Scale bar in FIG. 5F=50 μm and can be applied to FIG. 5E. Green signal in FIG. 5D represents fibronectin, red signal represents GFAP, and blue signal represents rhodamine B within fibers. Data in FIG. 5C represent mean values±SE from four independently prepared cultures. * indicates statistical significance.

(FIGS. 6A-C) 40× fluorescent images of individual neurons seeded on astrocytes which were cultured on aligned fiber scaffolds (FIG. 6A), PLLA films (FIG. 6B), or fiber/AFFT scaffolds (FIG. 6C). (FIGS. 6D-F) Isolated traces of individual neurons pictured in FIG. 6A, FIG. 6B, and FIG. 6C, respectively. (FIGS. 6G-I) Polar histograms showing total outgrowth and orientation of neurites seeded on astrocyte layers which were cultured on the three scaffold types (FIG. 6G=aligned fibers, FIG. 6H=film, FIG. 6I=fibers with AFFT). Histogram I shows a transition from aligned neurite growth (right of histogram) to unaligned growth (left) upon neurite growth into AFFT boundary. Scale bars in FIGS. 6A-F=50 μm. Green signal in fluorescent images represents GFAP, red signal represents neurofilament, and blue signal represents rhodamine B within fibers. White line in FIG. 6G marks the beginning of the fiber-free gap.

(FIG. 7A) Comparison of total neurite length shows significantly greater length on aligned fibers than on films or AFFT scaffolds ($p<0.05$). (FIG. 7B) Comparison of single longest neurite length (black) and average longest neurite length (gray). Average longest neurites are significantly longer on aligned fibers ($p<0.05$) than other two scaffolds. Data for all plots taken from three independent cultures. * signifies statistical significance.

(FIGS. 8A-E) 40× magnification images of neurites which either failed to grow into AFFT region (FIG. 5A), or grew: less than 50 μm (FIG. 8B), between 50 and 100 μm (FIG. 8C), between 100-150 μm (FIG. 8D), or greater than 150 μm into AFFT (FIG. 8E). No neurite growth greater than 200 μm into AFFT was seen. (FIG. 8F) Quantification of the proportion of neurites that grew within each distance bin in AFFT. Scale bar in FIG. 8A=25 μm, while the scale bar in FIG. 8E=50 μm and can be applied to FIG. 8B, FIG. 8C, and FIG. 8D. Blue signal in (FIGS. 8A-E) represents rhodamine B present in fibers, while red signal represents neurofilament. Rhodamine-derived blue signal is present in AFFT region due to the dissolution of fluorescently labeled fibers. Data in FIG. 8F are derived from analysis of 21 individual neurons, all seeded within 50 μm of AFFT boundary.

(FIG. 9A) AFM image of beginning of AFFT boundary. Fibers (right) begin to melt (left). Line of analysis shown in black. (FIG. 9B) AFM image taken further into AFFT region showing remnants of melted fibers (right) melting into film (left). Line of analysis in black. (FIGS. 9C-D) AFM graphs of scaffold height along analysis lines shown in FIG. 9A and FIG. 9B, respectively. Blue dots in graphs correspond to location of blue dots in FIG. 9A and FIG. 9B.

(FIG. 10A) 20× fluorescent image of astrocytes seeded onto fiber/AFFT scaffolds. (FIGS. 10B, C) Magnified view of single astrocytes on aligned fibers (B) and in AFFT (FIG. 10C) with cell edges traced for emphasis. Scale bar in FIG. 10A=100 μm, while scale bar in FIG. 10B=50 μm and can be applied to FIG. 10C. All grayscale signal represents GFAP.

(FIGS. 11A-D) The nebulized solvent spray method was used to create a diamond pattern (FIG. 11A), a circle (FIG. 11B), a triangle (FIG. 11C), and a square (FIG. 11D) Scale bar in FIG. 11A=1 mm and can be applied to FIG. 11B, FIG. 11C, and FIG. 11D.

DETAILED DISCLOSURE OF THE INVENTION

Developing robust in vitro models of in vivo environments has the potential to reduce costs and bring new therapies from the bench top to the clinic more efficiently. The present invention develops a biomaterial platform capable of modeling isotropic-to-anisotropic cellular transitions observed in vivo, for example, changes in cellular organization following spinal cord injury.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animal models. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The present invention provides cell culture devices, and related kits and methods, for modeling isotropic-to-anisotropic cellular transitions that are observed in injured tissues, such as for example, spinal cord injury, tendon injury, and muscle injury. Biomaterial constructs possessing topographical and non-topographical domains with a subset of cells, such as cells found within the spinal cord, may be used to assess the efficacy of pharmacological agents or to understand changes in cellular physiology at anisotropic-to-isotropic transitions without great difficulty or expense of time. Aspects of the present invention provide anisotropic-to-isotropic fiber/film transition (AFFT) boundaries within electrospun scaffolds depictive of, e.g., structural changes that result following white matter spinal cord ischemia (SCI).

Figure 1:
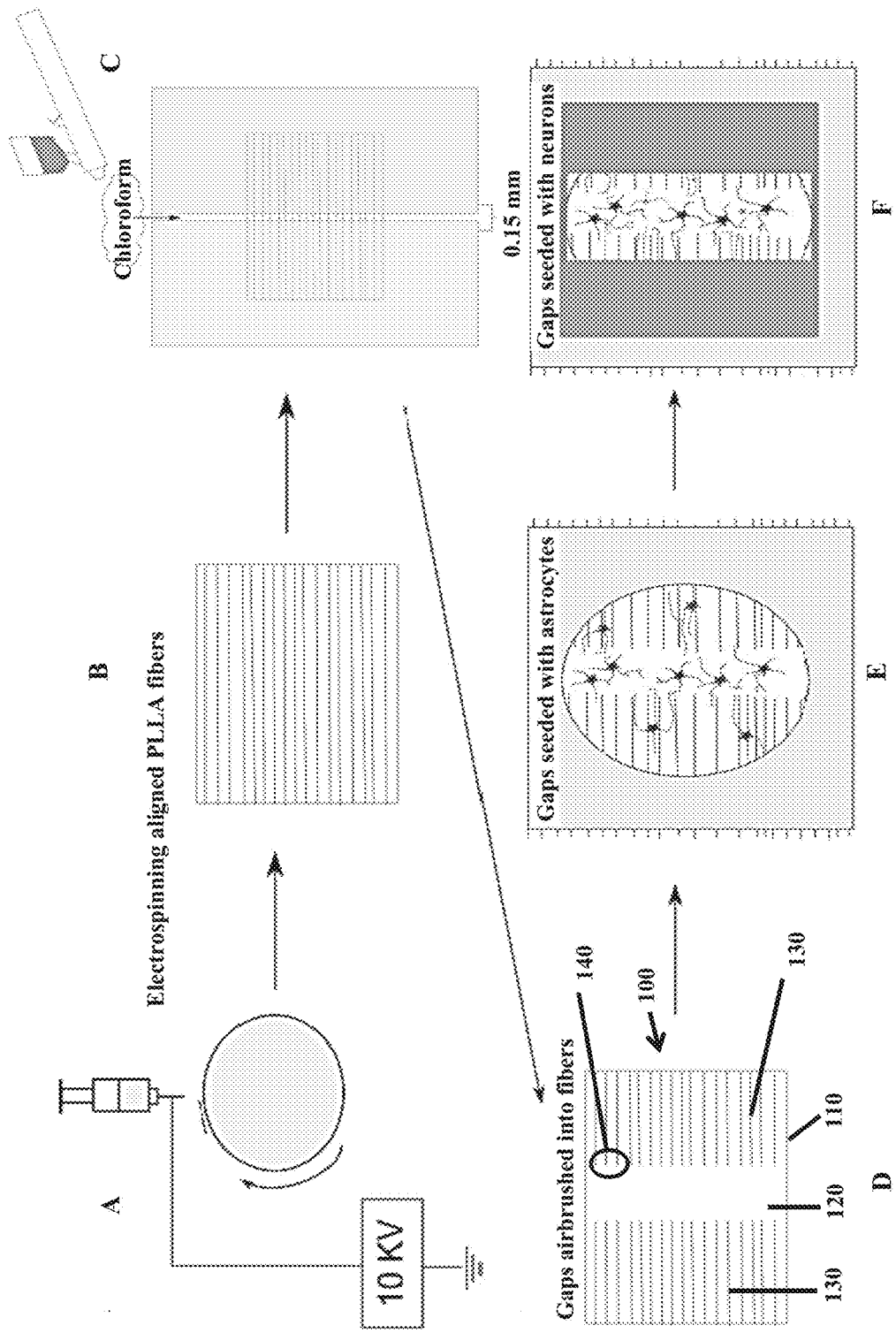
FIG. 1 shows a schematic of electrospun fiber fabrication, patterning, and cell co-culture. Aligned fibers were fabricated via electrospinning with 10 kV of applied potential (A-B). Airbrushing with nebulized chloroform (C) results in fiber-free regions (D). Astrocytes (E), followed by neurons (F), were cultured on processed fiber scaffolds using polydimethylsiloxane (PDMS) molds.
Figure 2A:
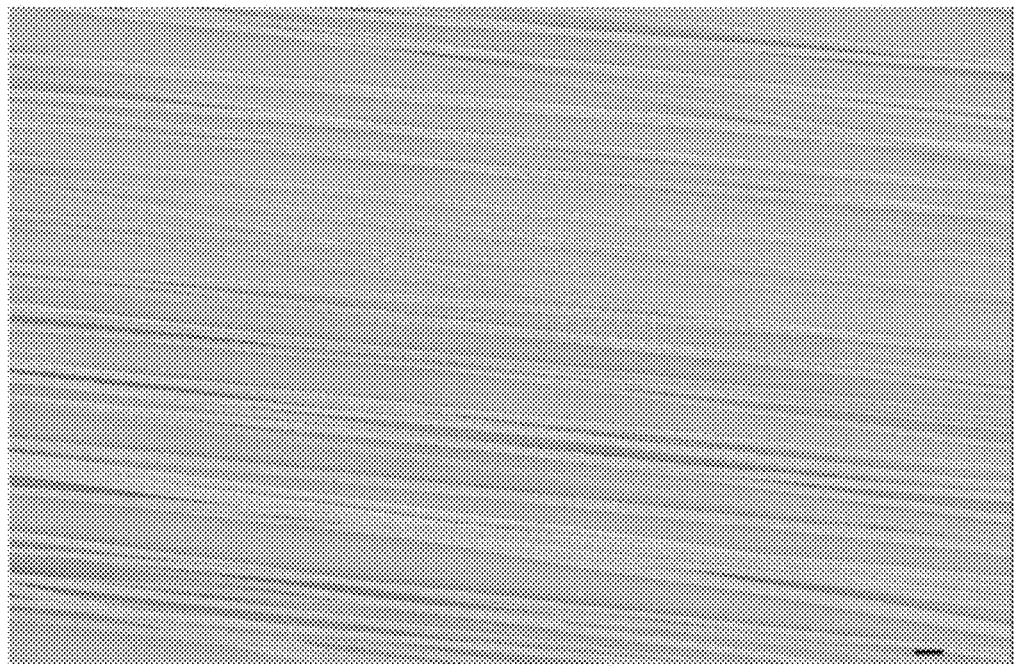
FIGS. 2A-E show the characterization of poly-L-lactic acid (PLLA) fiber/anisotropic-to-isotropic fiber/film transition (AFFT) scaffolds.
Figure 2B:
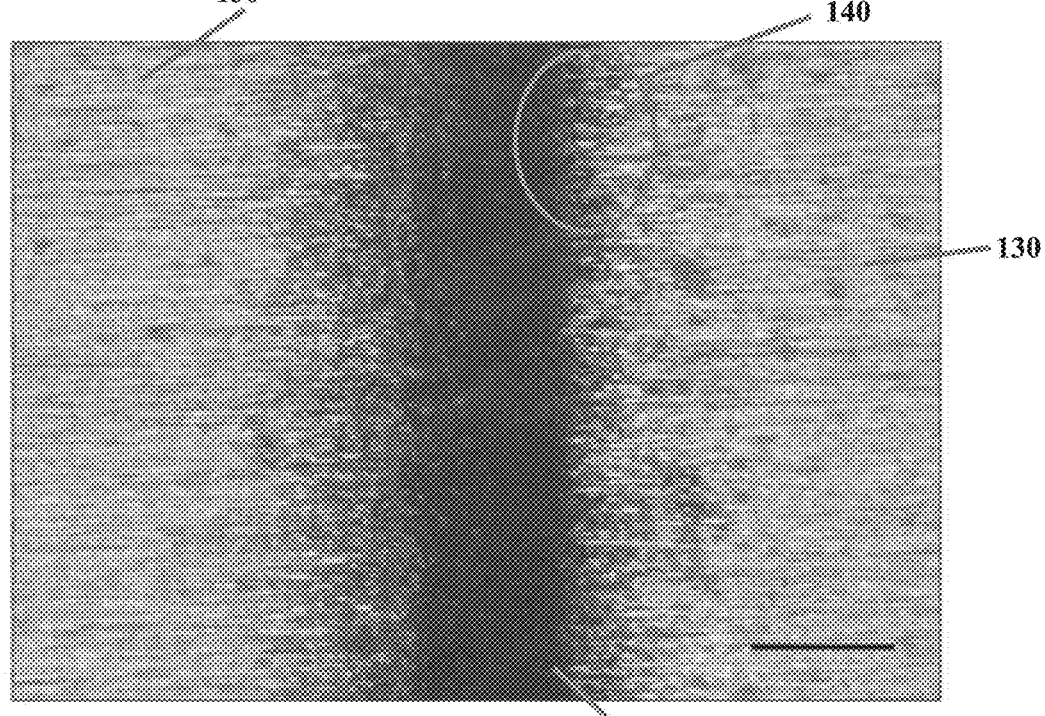
Figure 3A:
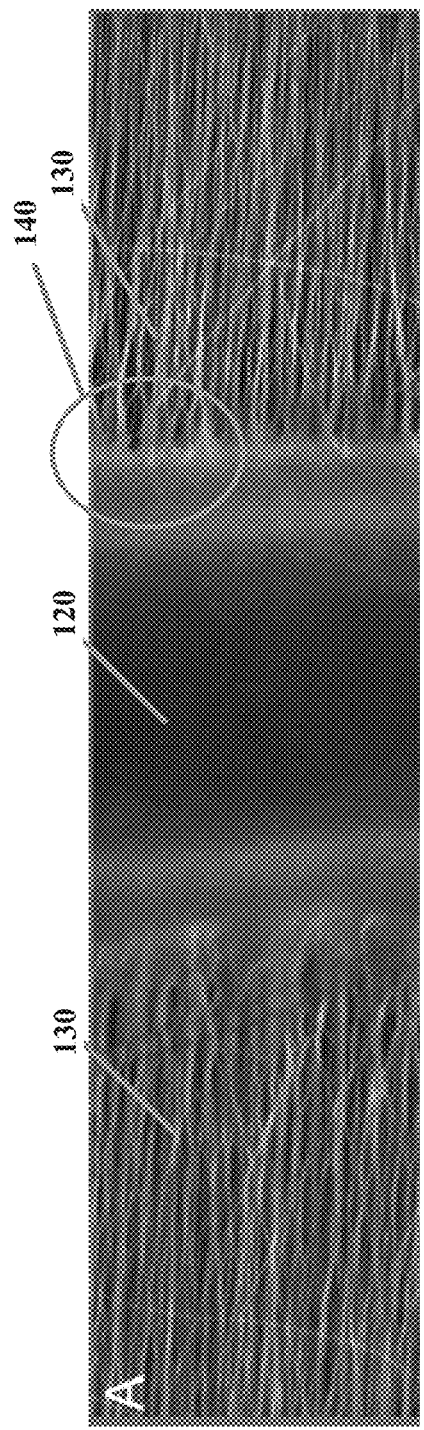
FIGS. 3A-D illustrate that astrocytes cultured on fiber/gap scaffolds show varying alignment depending on their location on the scaffold.

In one aspect, and as illustrated in FIGS. 1D, 2B, and 3A, the present invention provides a cell culture apparatus 100 for modeling isotropic-to-anisotropic cellular transitions, comprising a substrate 110 comprising an isotropic film surface 120 with one or more regions of aligned fibers 130 dispersed thereon. The one or more regions of aligned fibers 130 and the isotropic film surface 120 provide a topographic-to-non-topographic transitional boundary 140 therebetween. In some embodiments, the fibers are electrospun fibers. In some embodiments, the fibers and/or isotropic film surface comprise poly-L-lactic acid (PLLA). In some embodiments, the transitional boundary between the aligned fibers and the isotropic film surface is at an end, lengthwise, of the respective aligned fibers. In some embodiments, the topographic-to-non-topographic transitional boundary is formed by selectively dissolving a portion of the aligned fibers.

In some embodiments, the transitional boundary runs perpendicular to the length of aligned fibers.

Further, the aligned fibers collectively form a scaffold, and the topographic-to-non-topographic transitional boundaries are positioned between each of the scaffolds. In some embodiments, the aligned fibers run perpendicular to the transitional boundaries.

In another aspect, and as illustrated in FIGS. 1A, B, and C, the present invention provides methods of fabrication of the cell culture apparatus of the present invention. The methods comprise depositing a collection film, such as, e.g., a PLLA film, onto a substrate; depositing fibers, such as, e.g., PLLA fibers, onto the collection film to form fiber scaffolds; and dissolving a portion of the fibers to yield one or more regions of an isotropic film surface that transition from the fiber scaffolds to form an anisotropic-to-isotropic fiber/film boundary. In some embodiments, each of the fibers are deposited such that they are aligned relative to each other. In some embodiments, the fibers are dissolved with chloroform, particularly nebulized chloroform, to yield an isotropic surface. In some embodiments, the anisotropic-to-isotropic fiber/film boundary is at an end, lengthwise, of where the respective fibers are dissolved.

The fibers utilized in the methods and devices described herein may be produced by electrospinning techniques. Electrospinning is a technique producing either randomly oriented or aligned fibers with essentially any chemistry and diameters ranging from 15 nm to 10 μm. The fibers produced in preferred embodiments of the present invention are aligned.

In one embodiment, nebulized solvent patterning of electrospun fiber substrates is utilized. This method of patterning electrospun fibers on a substrate comprises providing an isotropic substrate with electrospun fibers thereon (the fibers may be aligned or, alternatively, non-oriented); contacting the fibers with a nebulized solvent; and dissolving the fibers at desired locations on the substrate to yield a specific pattern, wherein a topographic transitional boundary between the fibers and the substrate is formed. If PLLA fibers are to be patterned, nebulized chloroform is utilized as the solvent. This method produces a clear topographic transitional boundary between aligned PLLA fibers and an isotropic PLLA film region.

In another aspect, the present invention provides methods of modeling in viva cellular response to isotropic-to-anisotropic topographic transitions in an in vitro model for tissue injury. The methods comprise providing a cell culture apparatus as described herein; seeding one or more cells onto the substrate; allowing the cells to adhere to the one or more regions of aligned fibers; and allowing the cells to grow, whereby cell growth within the transitional boundary between the aligned fibers and the isotropic film surface models in vivo cell growth in isotropic-to-anisotropic topographic transitions of injured tissue. In some embodiments, the cells utilized in the methods provided herein are derived from neural tissue.

As would be understood by those of skill in the art, the cells utilized are dependent on the type of tissue injury being analyzed. For example, spinal cord injuries may require neuron and astrocyte cell culture, or, for example, skin injuries may require one or more of keratinocytes, melanocytes, Merkel's cells, and Langerhans cells.

In yet another aspect, the present invention provides kits for examining cellular response to isotropic-to-anisotropic topographic transitions, comprising a cell culture apparatus of the present invention; and one or more reagent. The kits may further be used in the methods described herein. The kits may also include instructions for their use. Also, the kit may include one or more containers filled with reagent(s) and/or one or more components, such as, e.g., cell culture media. One or more container of the kits provided may also comprise a drug or other pharmaceutical composition that is being tested for effects on the cellular response to isotropic-to-anisotropic topographic transitions.

In certain embodiments, the kits may additionally include reagents and means for detecting one or more cellular components. The means of allowing detection may be by conjugation of detectable labels or substrates, such as fluorescent compounds, enzymes, radioisotopes, heavy atoms, reporter genes, luminescent compounds, or antibodies against the cellular component of interest. As it would be understood by those skilled in the art, additional detection or labeling methodologies may be used in the kits provided.

As would be understood by those of skill in the art, the methods, devices, and kits of the present invention are contemplated to be applicable to in vitro modeling of cellular responses of in vivo tissue injuries. Such injuries include, but are not limited to, spinal cord injuries, muscle injuries, tendon or ligament injuries, and skin injuries.

The subject invention includes, but is not limited to, the following exemplified embodiments.

Embodiment 1

A cell culture apparatus for modeling isotropic-to-anisotropic cellular transitions, comprising:
  a substrate comprising an isotropic film surface with one or more regions of aligned fibers dispersed thereon, wherein the one or more regions of aligned fibers and the isotropic film surface provide a topographic-to-non-topographic transitional boundary therebetween.

Embodiment 2

The apparatus according to embodiment 1, wherein the fibers are electrospun fibers.

Embodiment 3

The apparatus according to any of embodiments 1-2, wherein the fibers comprise poly-L-lactic acid.

Embodiment 4

The apparatus according to any of embodiments 1-3, wherein the isotropic film surface comprises poly-L-lactic acid.

Embodiment 5

The apparatus according to any of embodiments 1-4, wherein the topographic-to-non-topographic transitional boundary is formed by dissolving a portion of the aligned fibers.

Embodiment 6

A method of fabrication of a cell culture apparatus comprising fiber scaffolds for modeling isotropic-to-anisotropic cellular transitions, comprising:
  depositing a collection film onto a substrate;
  depositing fibers onto the collection film to form fiber scaffolds; and
  dissolving a portion of the fibers to yield one or more regions of an isotropic film surface that transition from the fiber scaffolds to form an anisotropic-to-isotropic fiber/film boundary.

Embodiment 7

The method according to embodiments 6, wherein the fibers are aligned.

Embodiment 8

The method according to any of embodiments 6-7, wherein the fibers are dissolved with chloroform.

Embodiment 9

The method according to any of embodiments 6-8, wherein the collection film comprises poly-L-lactic acid.

Embodiment 10

The method according to any of embodiments 6-9, wherein the fibers comprise poly-L-lactic acid.

Embodiment 11

A method of modeling in vivo cellular response to isotropic-to-anisotropic topographic transitions in an in vitro model for tissue injury, comprising:
providing an apparatus of any of embodiments 1-5;
seeding one or more cells onto the substrate;
allowing the cells to adhere to the one or more regions of aligned fibers; and
allowing the cells to grow, whereby cell growth within the transitional boundary between the aligned fibers and the isotropic film surface models in vivo isotropic-to-anisotropic topographic transitions of injured tissue.

Embodiment 12

The method according to embodiment 11, wherein the cells are derived from neural tissue.

Embodiment 13

A kit for examining cellular response to isotropic-to-anisotropic transitions, comprising:
an apparatus according to any of embodiments 1-5; and
one or more reagent.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The devices, methods, and kits herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

The following materials and methods were used for all the devices, methods, and kits exemplified herein.

Creation of Aligned Electrospun Fibers—

To create the aligned, electrospun fibers utilized in the present invention, collection films were first prepared. These films were made via the dissolution of 4 wt. % poly-L-lactic acid (PLLA) (NatureWorks, grade 6201D, Cargill Dow, Minnetonka, Minn.) in a 50:50 wt. % mixture of chloroform (EMD Millipore, Billerica, Mass.) and dichloromethane (Macron Chemical, Center Valley, Pa.). The solution was mixed continuously for 2 hours until full PLLA dissolution was observed. Afterward, the solution was deposited onto 15×15 mm, thickness #1 glass cover slips (Knittel Glass, Baunsenweig, Germany) and allowed to dry overnight.

To begin the process of electrospinning, 8 wt. % PLLA was dissolved at room temperature in a 50:50 wt. % mixture of chloroform and dichloromethane. This solution was then electrospun in accordance with procedures previously published by the Gilbert laboratory (Wang, et al., 2009; Wang, et al., 2010). Fibers were spun using a syringe with a 22 g sharp-tip needle (Fisher Scientific, Hampton, N.H.), which was insulated to establish high electrical charge only at the needle tip. A variable-speed syringe pump from Razel Scientific (St. Albans, Vt.) was used to continuously pump the PLLA solution at a rate of 2 mL/hr. The working voltage, supplied by a Gamma High Voltage Research power supply (Ormond, Fla.), was maintained at 10 kV. Fibers were collected onto collection films, which were attached to a spinning aluminum collection wheel (diameter 15 cm) using double sided tape (3M, St. Paul, Minn.). During electrospinning, the following protocols were employed: distance between the spinning disk and the needle tip was 6 cm, fiber collection time was 20 minutes, ambient humidity and temperature was controlled between 32-45% and 18-25° C. respectively. For experiments where fibers were to be visualized using epifluorescence microscopy, 10 μg of rhodamine-B (Sigma-Aldrich) was added to the electrospinning solution prior to fiber fabrication. Fluorescent fibers were kept isolated from light until cell seeding.

Creation of AFFT Boundary Electrospun Fiber Scaffolds—

Smooth, isotropic film domains were created within the PLLA fiber scaffolds with nebulized chloroform using an airbrushing technique (FIG. 1). First, two 7.5 cm×2.5 cm glass microscope slides (Electron Microscopy Sciences, Hatfield, Pa.) were arranged parallel to each other. These slides were then separated by the width of one thickness #1 glass cover slip (approximately 150 m). Aligned, PLLA fiber samples were then placed 2 cm beneath the gap separating these slides, with fibers oriented perpendicular to the gap. This 2 cm distance prevented direct contact between fibers and slides, preserving fiber alignment. Chloroform was then airbrushed over the glass slides, selectively dissolving the fibers underneath the gap and creating smooth, isotropic film domains within the aligned fiber scaffolds. After treatment with nebulized chloroform, fiber scaffolds were sterilized for 12 hours via ethylene oxide.

Imaging and Analysis of AFFT Boundary Domains and Fiber Alignment Following Nebulization—

There was concern that nebulization would affect the alignment of fibers near the AFFT boundary. To analyze fiber alignment near the nebulization zone, scanning electron microscopy (SEM) was conducted. SEM micrographs were captured using a Carl Zeiss Supra55 setup with Direct Write Attachment. The fiber samples were attached to glass cover slips using conductive copper tape (3M), scaffold edges were secured to the copper tape using Pelco® Colloidal Silver Liquid (Ted Pella Inc., Redding, Calif.), and a Denton Desk IV Sputterer (Denton Vacuum, Moorestown, N.J.) was used to coat the fiber samples with a 5 nm conductive coating of platinum. Following preparation of fiber scaffolds, SEM micrographs were captured using a 6.6 mm working distance, 20 μm aperture diameter, and a 1.5 kV accelerating voltage. Images were captured using a 3:1 mixing ratio of an in-lens secondary electron detector and a Robinson backscattered electron detector. The resolution of all images was enhanced using line integration scanning (n=50 per line) at a reduced scanning rate.

Fiber diameter, density, and alignment were measured using ImageJ software (National Institutes of Health, Bethesda, Md.). Images of five unique scaffolds were used to take these measurements (n=5). To characterize possible effects of nebulized chloroform on fibers, images were taken both near (within 50 μm) and far (greater than 300 μm) from the AFFT boundary. In order to reduce bias, fibers were chosen for measurement using an objective procedure for all measurements. First, a vertical line 200 μm in length was drawn at the geometric center of each image. To measure alignment, the 15 fibers crossing closest to the center of the vertical line were traced. The angle measurements of these fibers were then averaged to find the mean angle of alignment. Differences between this mean and the unique angles of each of the 15 fibers were then found. Differences in alignment were sorted into bins of 2°. To measure fiber diameter, lines were drawn across 20 fibers closest to the center of the vertical reference line. The 20 diameters were then averaged. The density of the PLLA fibers was also measured using Image J. To measure density, a 100 μm reference line was drawn perpendicular to the direction of fiber alignment in the center of each image. Fibers completely crossing this reference line were then counted manually.

There was concern following nebulization that there would be a significant height difference between the fibers and the nebulized area that may subsequently affect neurite outgrowth from the fibers to the film. Thus, the AFFT boundary was analyzed using atomic force microscopy (AFM). Images of the boundary were captured using an Asylum Research MFP 3D AFM (Asylum Research, Goleta, Calif.). Two independent scaffolds were imaged using AFM, with three 78×78 μm images taken along the AFFT boundary of each. Changes in the height of individual fibers in each image were analyzed as the fibers dissolved into films within the AFFT.

Astrocyte Isolation and Culture—

Primary astrocyte cultures from the cerebral cortex of P2 Sprague-Dawley rat pups were isolated as previously described (Mongin et al., 2011) and in accordance to protocols approved by Rensselaer Polytechnic Institute's Institutional Animal Care and Use Committee (IACUC). Briefly, P2 rat pups were euthanized by rapid decapitation. The cerebral cortices were then separated from the meninges, hippocampi, and basal ganglia. The cortical tissue from four animals was minced and transferred to a solution containing TrypLE (Invitrogen, Carlsbad, Calif.) and OptiMEM (Invitrogen) at a 1:1 dilution. Cells were extracted using three 10-minute incubations with TrypLE/OptiMEM additionally supplemented with DNase 1 (Sigma-Aldrich, St. Louis, Mo.). The second and third extractions were combined with DMEM containing 10% heat inactivated horse serum (HIHS) and 50 U/mL penicillin plus 50 g/mL streptomycin (P/S, Invitrogen). Cells were pelleted using centrifugation (0.5 RCF for 5 minutes) and resuspended in an 89/10/1 vol % mixture of Dulbecco's Modified Eagle Medium (DMEM, Gibco, Grand Island, N.Y.), heat inactivated horse serum (HIHS, Invitrogen, Carlsbad, Calif.), and penicillin/streptomycin (Invitrogen). Dissociated cells were plated at a density of 200,000 cells/flask on poly-D-lysine (Sigma-Aldrich) coated T75 flasks. Flasks were coated for one hour in a 10 g/mL solution of poly-D-lysine in Hank's Balanced Salt Solution (HBSS, Gibco) and then washed twice with sterile distilled water prior to astrocyte plating. Astrocytes used in the study were cultured for 2-4 weeks prior to use in experiments. Some cells from each astrocyte isolation were plated onto 15 by 15 mm cover slips coated with poly-D-lysine using methods stated previously to determine astrocyte purity. Only T75 flasks were utilized where the corresponding astrocytes cultured on the glass cover slips contained an astrocyte purity >95%. An astrocyte was confirmed as being an astrocyte using an anti-glial fibrillary acidic protein (GFAP) stain (Dako, Carpinteria, Calif.). The specific staining procedure used is presented in the Immunocytochemistry section of the materials and methods described herein.

Culture of Astrocytes on AFFT Boundary Scaffolds—

Initially, sterilized PLLA fiber scaffolds were coated with fibronectin (20 μg/mL), since it was previously observed astrocytes strongly adhering to fibronectin coated fibers (Zuidema et al., 2014) However, in experiments presented here, astrocyte adhesion was observed to be less at the AFFT interface, so a different coating procedure was devised. In this study, sterilized PLLA scaffolds were coated with 250 μL of a 2:1 (v/v) mixture of poly-D-lysine (10 μg/mL, Sigma-Aldrich) and fibronectin (10 μg/mL, Sigma-Aldrich) in Hank's Balanced Salt Solution (HBSS, Gibco). The mixture was applied and allowed to coat for one hour at room temperature in a sterile biological hood. The coating solution was then removed, and samples were washed twice with 250 μL of sterile distilled water. Astrocytes were removed from culture flasks with TrypLE (Invitrogen) and resuspended in astrocyte media. Astrocytes were then seeded onto the PLLA scaffolds at a density of 300,000 cells/cm$^2$ and cultured in an incubator for 24 hours in 250 μL of astrocyte media. After 24 hours, 750 μL of astrocyte media was added to each culture, and astrocytes were incubated for an additional 72 hours. Astrocytes were concentrated around the AFFT boundaries via the use of polydimethylsiloxane (Dow Corning, Midland, Mich.) molds.

Neuron Isolation and Co-Culture with Astrocytes—

Neurons were isolated from the dorsal root ganglia (DRG) of P2 Sprague-Dawley rats according to previously established protocols (Koppes et al., 2011) and in accordance to protocols approved by Rensselaer Polytechnic Institute's Institutional Animal Care and Use Committee (IACUC). Briefly, DRG were digested for 50 minutes in a solution of 0.1 trypsin (MediaTech Inc., Manassas, Va.) and 1 mg/mL collagenase A (Sigma-Aldrich) in HBSS. The DRG were then further digested for ten minutes in a solution of 0.1% trypsin in HBSS and centrifuged at 100 g. Following centrifugation, DRG were titrated mechanically fifteen times via pipette. Dissociated neurons were preserved at a density of $10^6$ cell s/mL at a temperature of −80° C. until use.

After allowing the astrocytes to attach to the electrospun fiber scaffolds for 96 hours using methods described herein, neurons were introduced to the electrospun fiber scaffolds. Dissociated rat neurons were first centrifuged for two minutes at 2000 rpm. During centrifugation time, astrocyte media was removed from the astrocyte/electrospun fiber scaffolds. After being centrifuged, neurons were mixed with neural growth media. Neural growth media was made in 50 ml, increments via a 97/2/1 vol. % mixture of neurobasal media (Invitrogen), B-27 supplement (Life Technologies, Carlsbad, Calif.), and penicillin/streptomycin (Gibco). To this mixture, 3.7 mL of L-glutamine (Gibco) was added. Neurons were seeded onto astrocytes at a density of 80,000 cells per sample with 150 µL of neural growth media. Care was taken to seed all neurons within 3 mm of the edge of the non-topographical region via the use of polydimethylsiloxane molds. After two hours, 850 µL of neural growth media was added to each sample. Astrocyte/neuron co-cultures were then maintained for 24 hours in a tissue culture incubator.

Immunocytochemistry—

To visualize astrocytes and neurons following experimentation, the following immunocytochemistry approaches were used. After culture, samples were fixed with a 4% w/v mixture of paraformaldehyde (Sigma-Aldrich) in phosphate buffered saline (PBS) (Invitrogen) for one hour. Samples were then washed three times with PBS and blocked with a solution consisting of 5% bovine serum albumin (BSA, Sigma-Aldrich) and 0.4% Triton-X (Sigma-Aldrich) in PBS. After removal of the blocking solution, the samples were treated overnight at 4° C. with a dilution of primary antibody stain in incubating solution. Incubating solution consisted of 0.5% BSA and 0.1% Tween-20 (Sigma-Aldrich) in PBS. Primary antibodies used included: rabbit anti-glial fibrillary acidic protein (DAKO Z033429-2; 1:700 dilution), mouse anti-CS56 (Sigma-Aldrich C8035; 1:500), chicken anti-fibronectin (Sigma-Aldrich GW20021F; 1:500), and chicken anti-neurofilament M (Millipore AB5735, 1:1000). After incubating overnight, the samples were washed three times with a 0.1% solution of Tween-20 in PBS. A secondary stain was then applied in a 1:1000 dilution in incubating solution. Secondary stains used included: donkey anti-mouse (Invitrogen Alexa Fluor 488), goat anti-rabbit (Invitrogen Alexa Fluor 660), and goat anti-chicken (Invitrogen Alex Fluor 488). After one hour on a shake plate set to 120 rpm at room temperature, samples were treated with a DAPI nuclear stain (Sigma-Aldrich) which was applied to the samples at a concentration of 1 µg/mL in PBS. Fifteen minutes after the application of the DAPI stain, the samples were washed twice with PBS and imaged. All images were obtained using an inverted Olympus IX-81 microscope (Olympus, Tokyo, Japan) and compiled using Adobe Photoshop software (Adobe, San Jose. Calif.).

Analysis of Astrocyte Morphology and the Organization of Astrocyte Extracellular Matrix—

The morphology of astrocyte structure and extracellular matrix output was analyzed using the Orientation J plug-in (Rezakhaniha et al., 2012) for ImageJ. Images from four unique astrocyte cultures were used for analysis (N=4). First, images were adjusted using the Threshold tool to remove background fluorescence. Each image was then divided into a grid system using square bins of 50×50 µm. Using OrientationJ, the content of each bin was analyzed for directional morphology. In scaffolds with fiber-free isotropic domains, images acquired were centered upon the isotropic film region and included at least 300 µm of aligned fibers on each side of the AFFT boundary. On these images, analysis was first performed using 10 bins located 200 µm to the right of the right-most AFFT boundary. Next, 10 bins located on the right AFFT boundary were analyzed, followed by 10 in the geometric center of the isotropic film region. Finally, 10 bins were analyzed at the left boundary and 200 µm to the left of the left boundary, respectively. In images of the samples consisting entirely of fibers or of just films, each image was broken into 50 bins for analysis. Analysis was performed on GFAP to assess astrocyte morphology, and fibronectin (FN) and chondroitin sulfate proteoglycan (CSPG) were analyzed to assess extracellular matrix position and organization.

Measuring Neurite Extension in Astrocyte-Neuron Co-Cultures—

Neurite outgrowth from three unique co-cultures (cultures completed at three different points in time using different cells from separate astrocyte and neuron isolations) (N=3) was traced semi-automatically using Neurolucida software (MBF Bioscience, Wilmington, Vt.). Individual neurite length was calculated for each neuron after tracing. Additionally, the number of primary neurites (those originating directly from the soma) was calculated for each neuron. Finally, total neurite length and longest neurite were found for each image. Total neurite length was defined as the sum of lengths for each individual neurite, while the longest neurite was defined as the single longest neurite from base to tip.

Statistical Analysis—

Images from four cultures were chosen at random for the analysis of the three astrocyte factors (GFAP, FN, or CSPGs). For AFFT boundary scaffold samples, the average orientation of each factor in each portion of the scaffold was compared using one-way ANOVA testing with statistical significance defined at $p<0.05$. For analysis of neurite extension, 21 neurons were analyzed from each scaffold type (aligned electrospun fibers without a gap, aligned electrospun fibers with a gap, and a control without topography (PLLA film)). The average total neurite length and longest neurite, were compared using a student's t-test with statistical significance defined at $p<0.05$. All graphs were compiled using mean±standard error of the mean.

Example 1: Characterization of AFFT Boundary Scaffolds

Figure 2C:
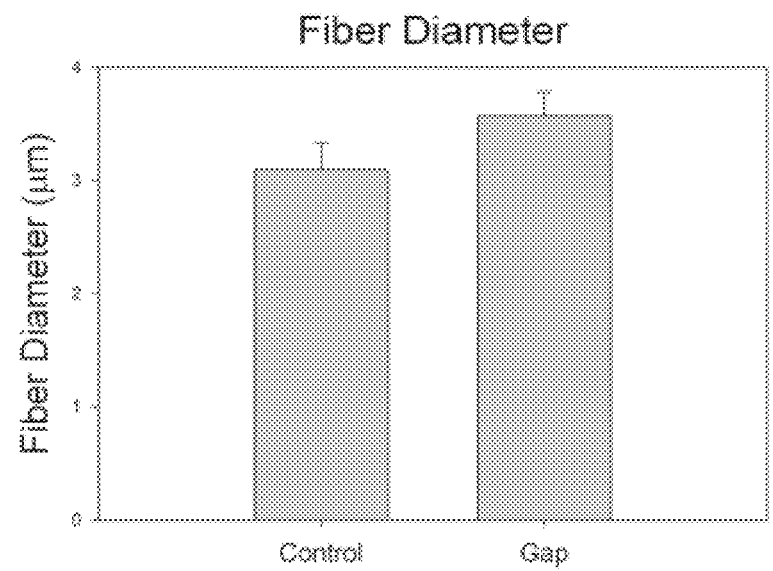
Figure 2D:
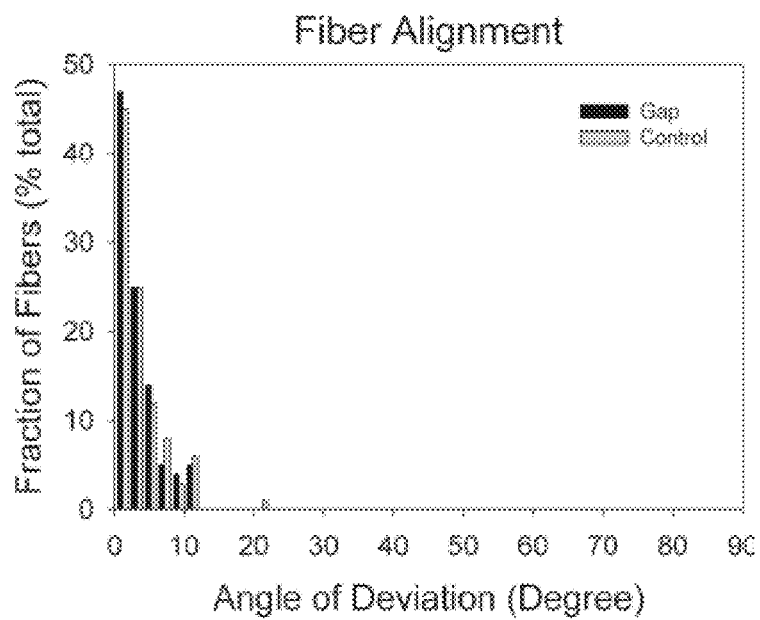
Figure 2E:
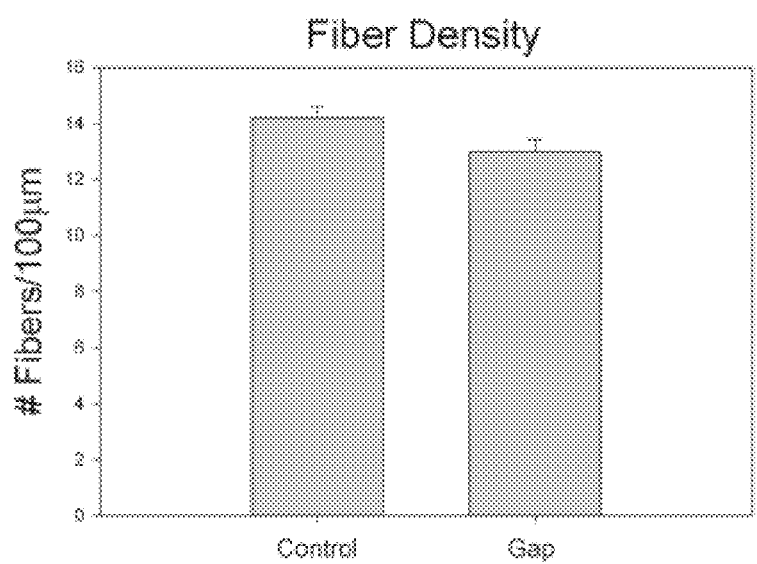
Figure 9A:
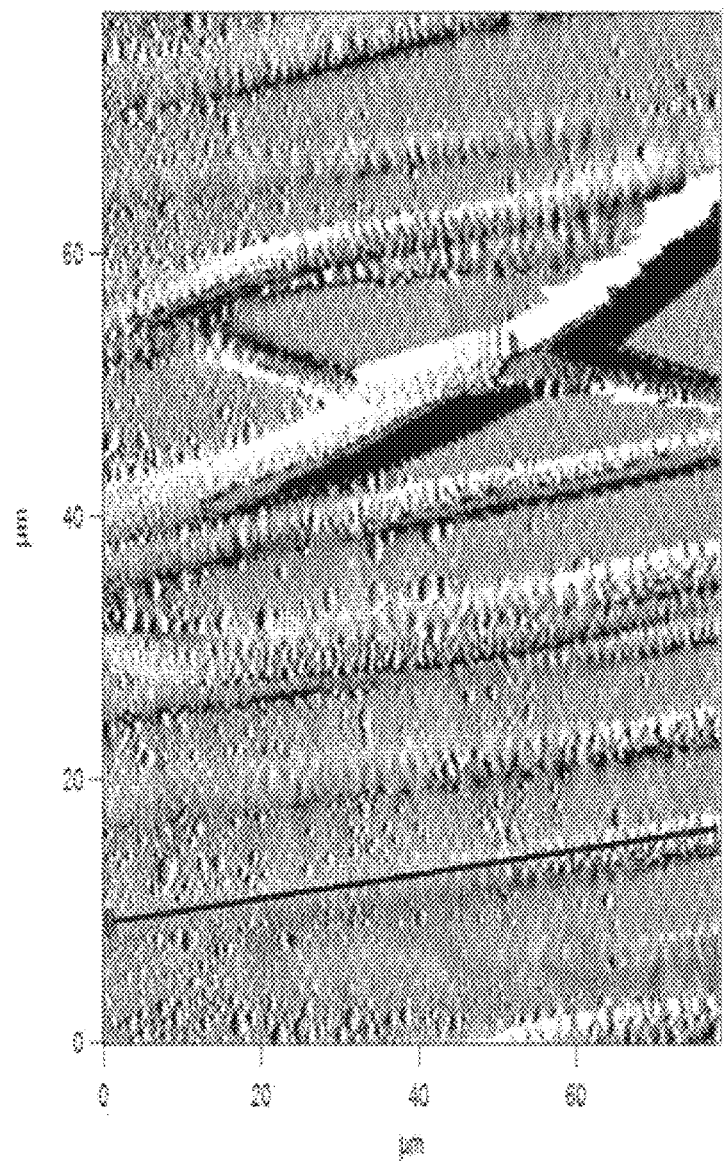
FIGS. 9A-D illustrate that selective dissolution of fibers shows a gradual change in scaffold thickness.
Figure 9B:
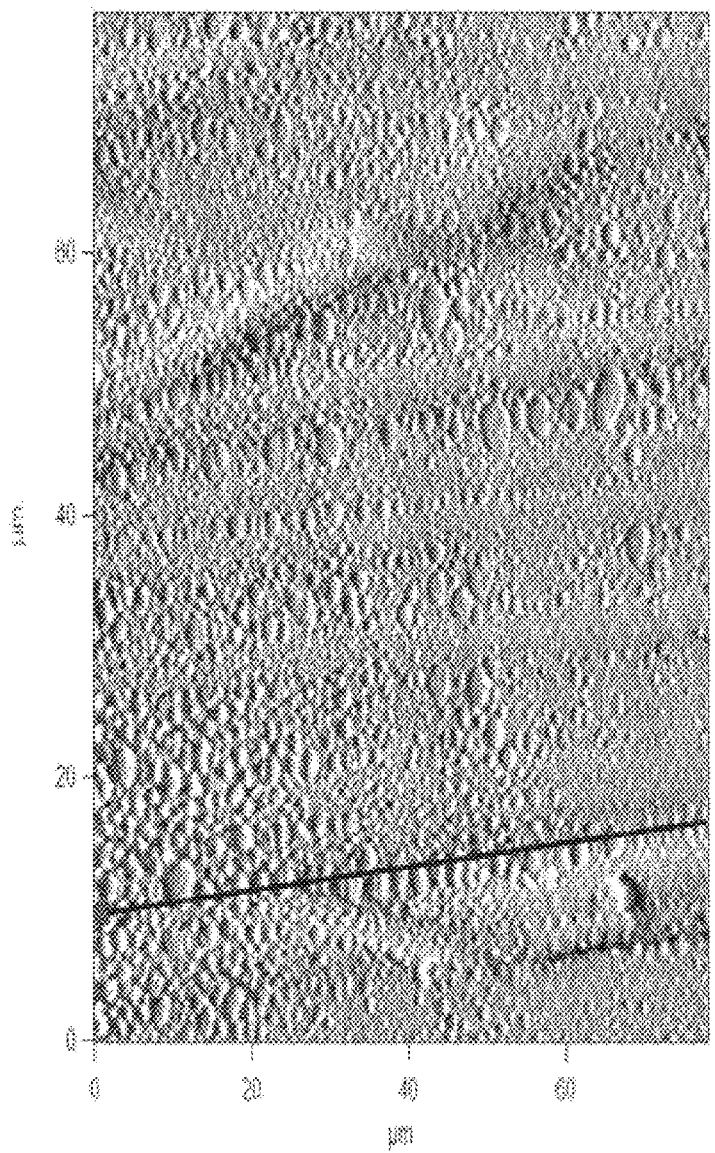
Figure 9C:
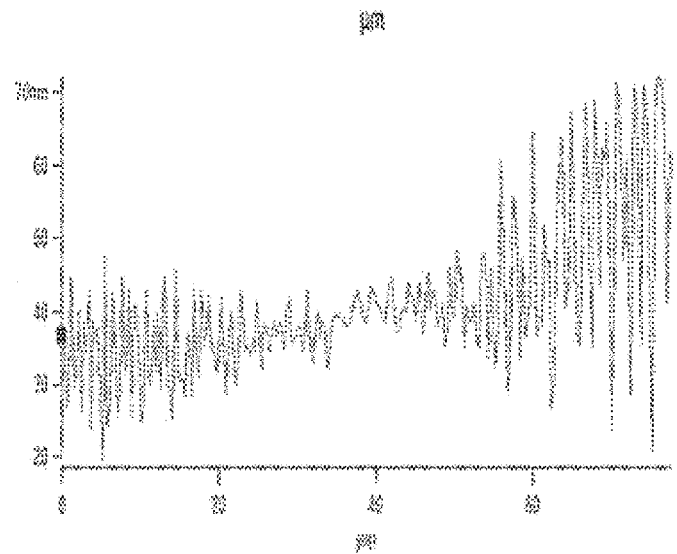
Figure 9D:
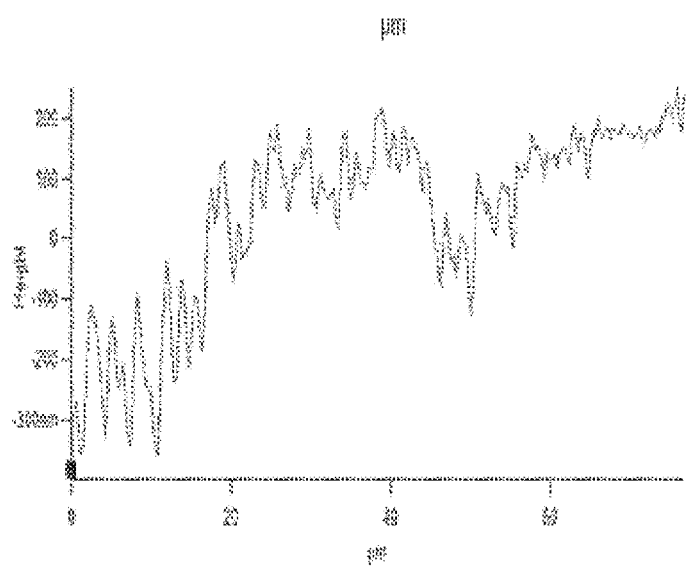

Since other studies show that neurites or neuronal cells respond to differences in fiber diameter (Wang et al., 2010; Christopherson et al., 2009), Applicants wanted to first verify that nebulization would not alter the physical properties of the fibers. Therefore, the fiber alignment and morphology of PLLA fiber scaffolds was characterized using three imaging techniques to reveal the general morphology of fibers and the isotropic film regions. MIA fibers (FIG. 2A) were imaged using a SEM to produce high magnification images revealing the alignment of fibers. A stereoscope was used to image the AFFT boundaries (FIG. 2B) at lower magnifications to show the overall size of the isotropic film region in the fibers. Fiber diameter, alignment, and density were then compared between control electrospun fiber scaffolds and electrospun fibers that had been subjected to nebulized chloroform. Fiber diameter was similar between the two groups as expected and nebulization did not appear to alter the diameter of the fibers. The average fiber diameter was 3.09±0.25 µm and 3.57±0.21 µm in the non-nebulized samples and in the nebulized samples, respectively (FIG. 2C). Fiber alignment was compared between the two groups and both groups were highly aligned with the vast majority of fibers being within 10 degrees from the median fiber angle (FIG. 2D). There were also no significant differences seen between the fiber densities of the two groups; the density was 14.2±0.37 fibers per 100 µm for the control fibers and 13±0.44 fibers per 100 μm for the fibers following creation of the AFFT boundary, respectively (FIG. 2E). These analyses demonstrate that the process of creating AFFT boundaries using nebulized chloroform does not affect the physical properties of the fibers except in the isotropic film region. The AFFT isotropic region width was also analyzed, and the average width was found to be 554.85±14.2 μm. Atomic force microscopy was used to determine how nebulized chloroform affected the scaffold height and scaffold surface (FIG. 9). There was a gradual decrease in height of 0.4 nm/μm at the beginning of the AFFT boundary (FIGS. 9A,C). Further into the AFFT boundary, the slope increased to 5 nm/μm (FIGS. 9B,D). These results demonstrate a very gradual change in the height of the scaffold.

Example 2: Astrocyte Morphology on AFFT Boundary Scaffolds

Figure 3B:
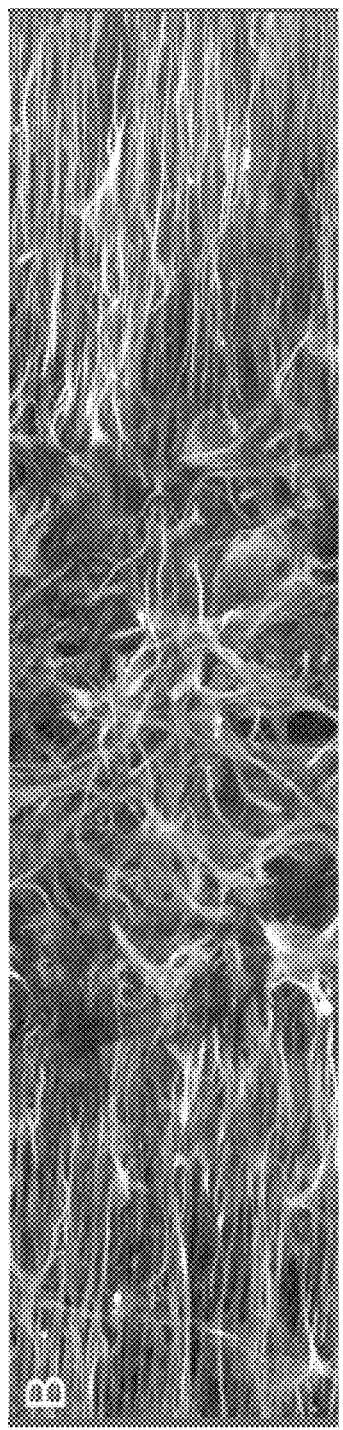
Figure 3C:
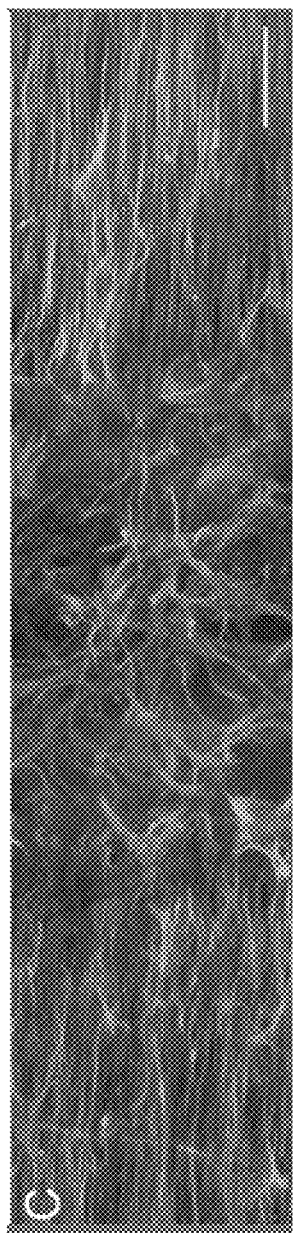
Figure 3D:
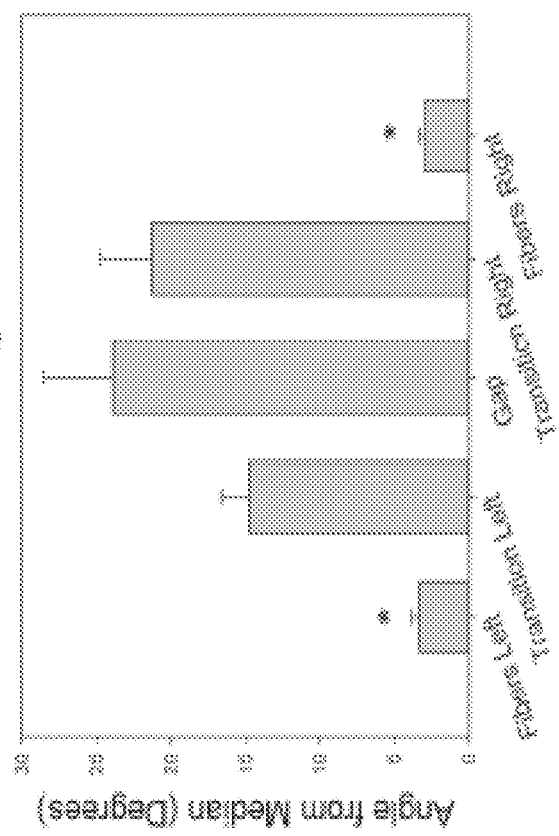
Figure 10A:
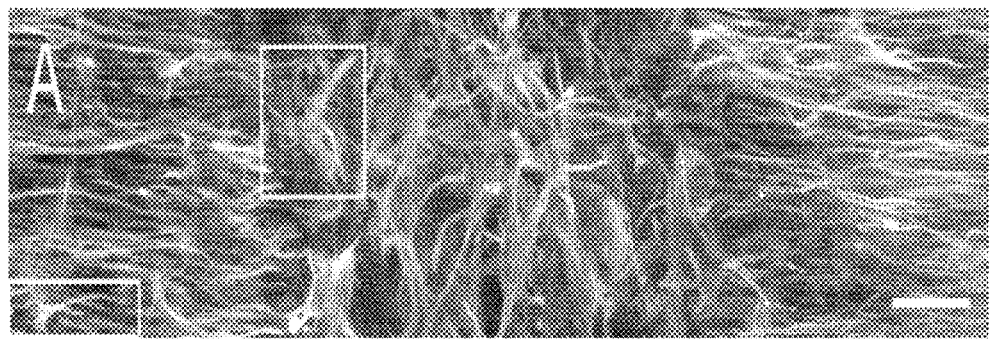
FIGS. 10A-C illustrate that astrocytes on fibers and in AFFT show markedly different morphology.
Figure 10B:
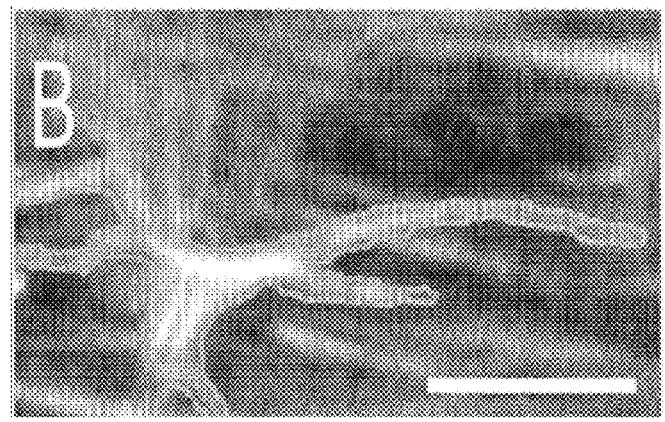
Figure 10C:
Figure 11A:
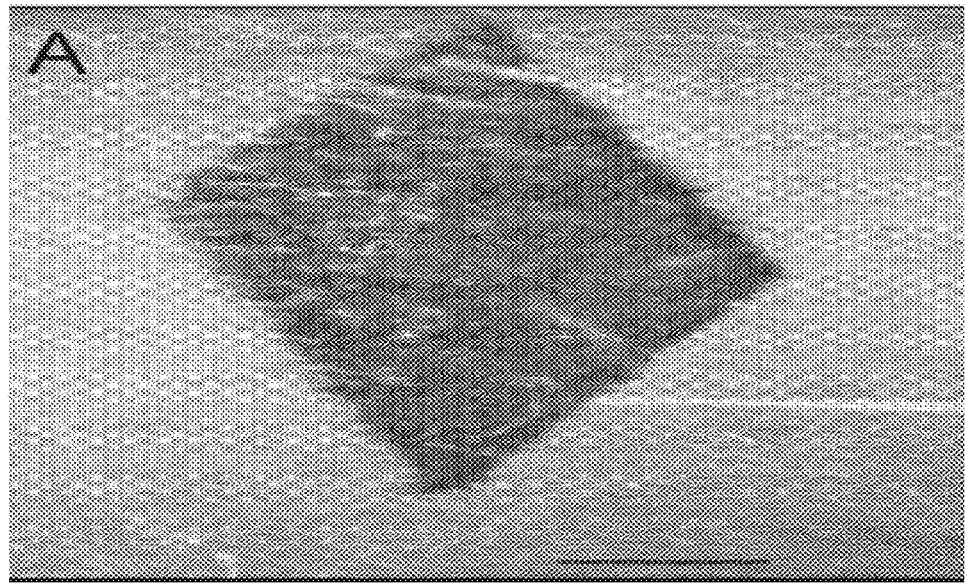
FIGS. 11A-D shows that nebulized chloroform can be used to create a variety of patterns in aligned PLLA fiber scaffolds.
Figure 11B:
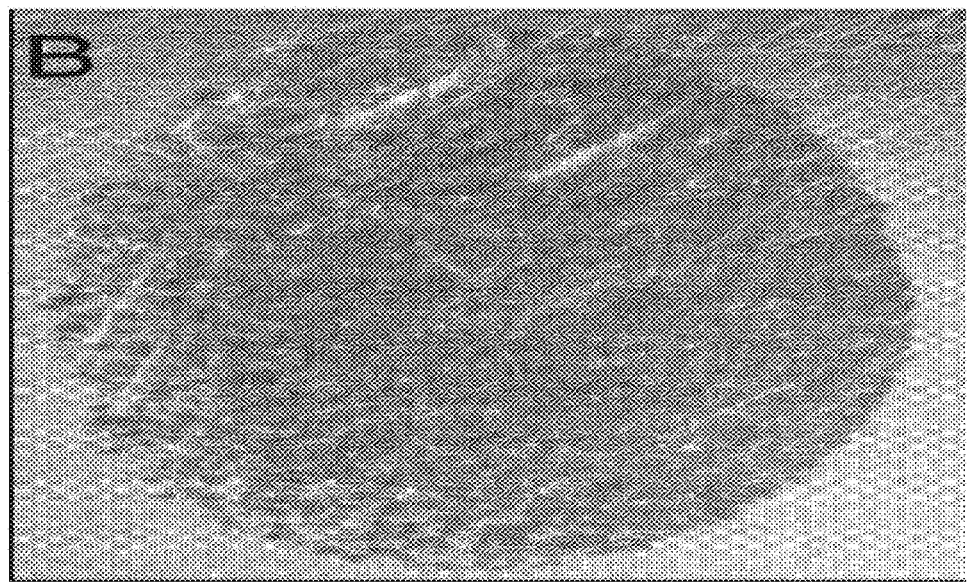
Figure 11C:
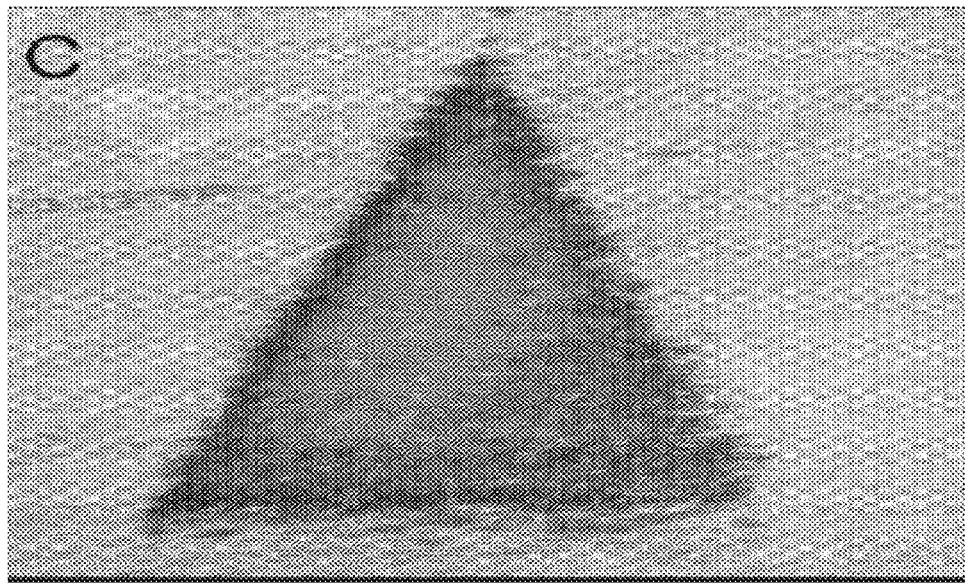
Figure 11D:
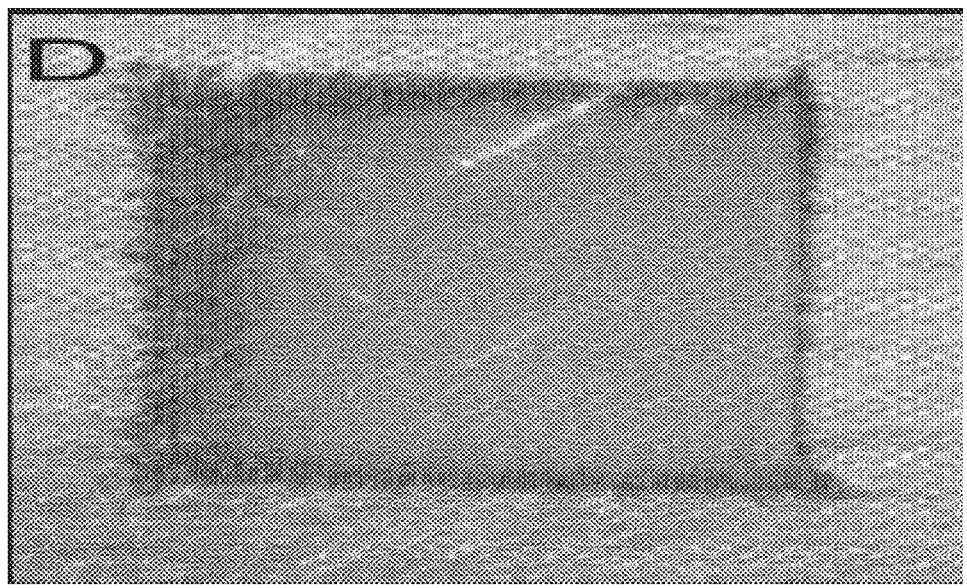

Once it was confirmed that nebulization did not alter fiber physical properties (alignment, diameter, and density) or sufficiently alter scaffold depth in nebulized regions, the ability of the scaffolds to promote cellular adhesion and to alter astrocyte morphology was determined. Astrocytes were imaged following four days in culture on fluorescent PLLA fibers (FIG. 3) to examine the ability of the AFFT boundary regions to influence astrocyte morphology. PLLA fibers were fluorescently labeled to show where the AFFT region started (FIG. 3A). Astrocytes were then stained against GFAP (FIG. 3B) and imaged to show the changes in their aligned orientation. The overlay of the images demonstrated that the astrocytes are aligned on the fibers while astrocytes in the isotropic film region show no preferential alignment (FIG. 3C). The orientation of the astrocytes was then determined at different distances into and before the AFFT boundary, revealing that astrocytes on the fibers were significantly more aligned than astrocytes located anywhere in the isotropic film region (FIG. 3D). Astrocyte morphology was also analyzed at higher magnifications (FIG. 10). Astrocytes growing on aligned fibers have processes that extend in the direction of fiber alignment (FIGS. 10 A,B). These processes also appear to take up a greater volume percentage of the cell compared to the astrocytes growing in the gaps (FIGS. 10 B,C). The astrocytes growing in the isotropic film region appear to have larger cell bodies, and their processes extend in all directions without preference (FIG. 10C). These images demonstrate that the AFFT boundary scaffolds can be used to create a transition where cells are oriented on the fibers but have no preferential orientation on the isotropic film regions of the AFFT boundary scaffolds.

Example 3: Astrocytes Orient Their ECM Along the Aligned PLLA Fibers

Figure 4A:
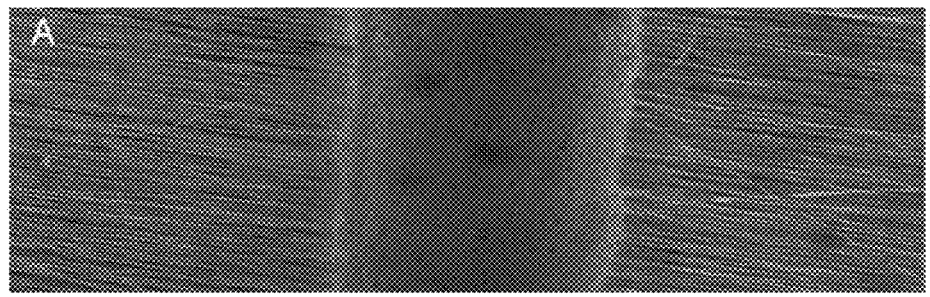
FIGS. 4A-G illustrate that alignment of astrocyte-produced CSPGs is disrupted within the AFFT.
Figure 4B:
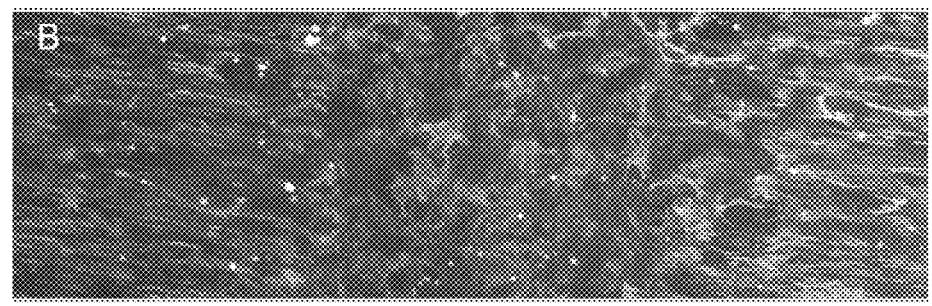
Figure 4C:
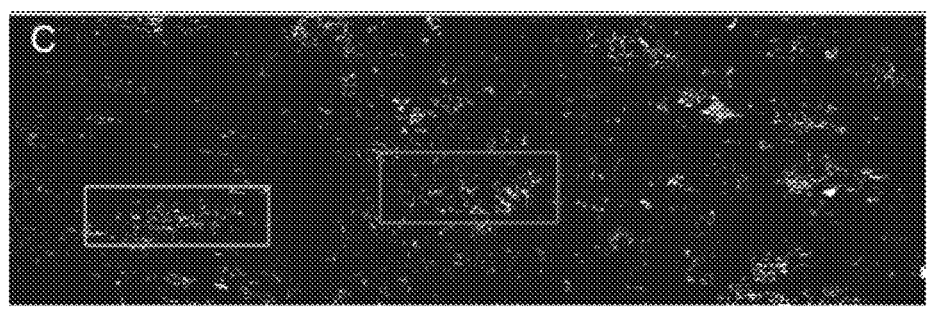
Figure 4D:
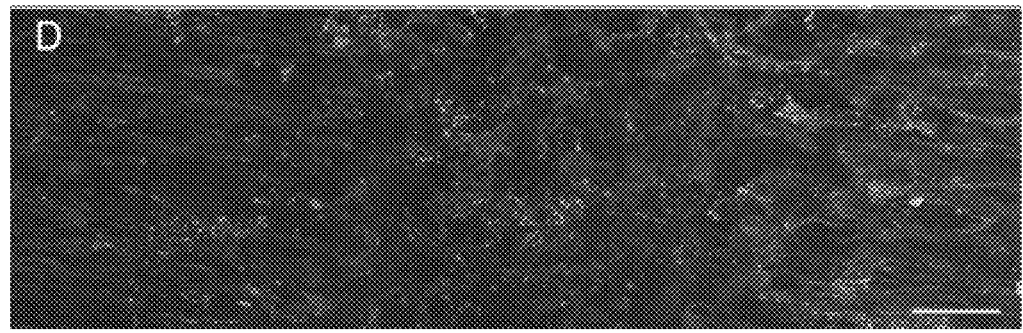
Figure 4E:
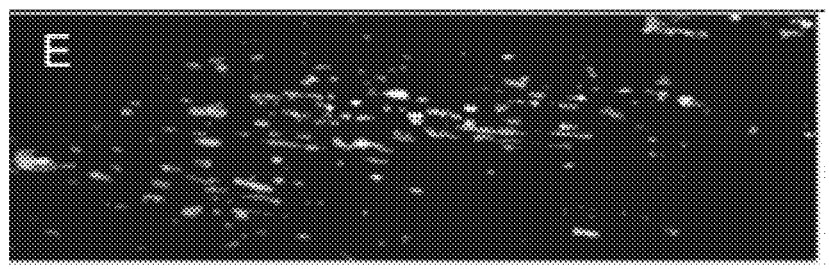
Figure 4F:
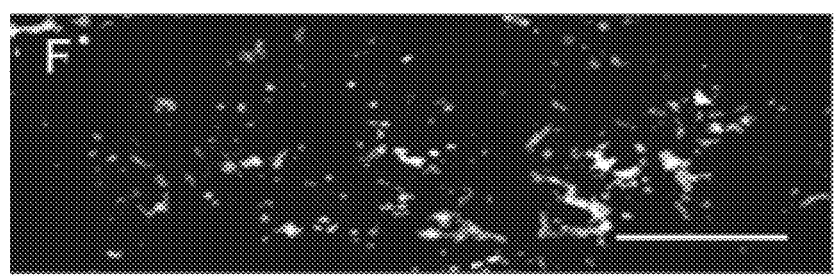
Figure 4G:
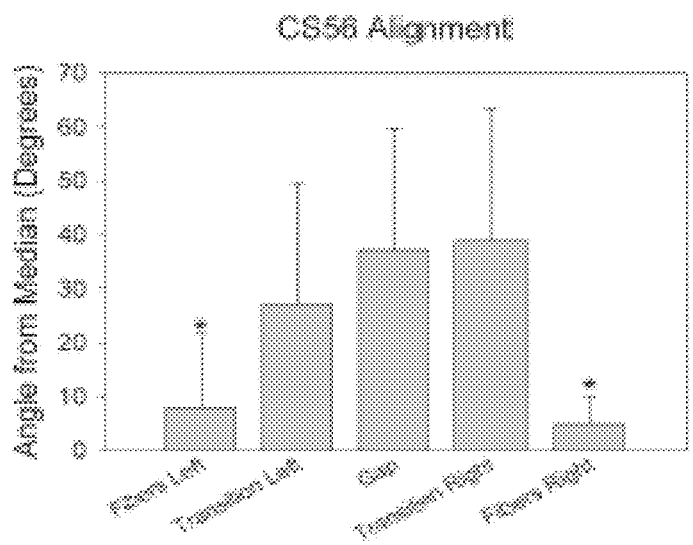
Figure 5A:
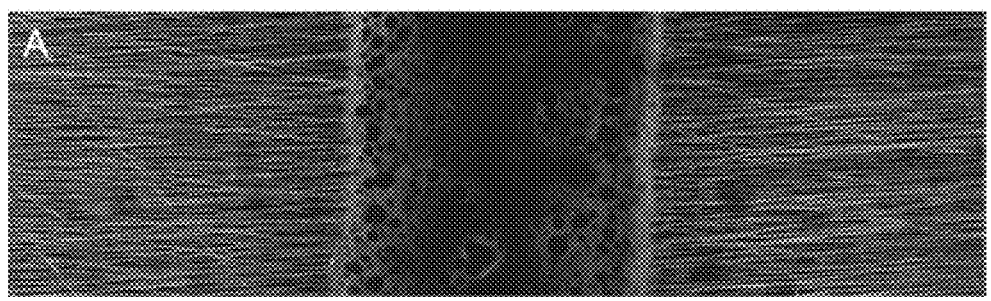
FIGS. 5A-G shows alignment of astrocyte-produced fibronectin is disrupted within the AFFT.
Figure 5B:
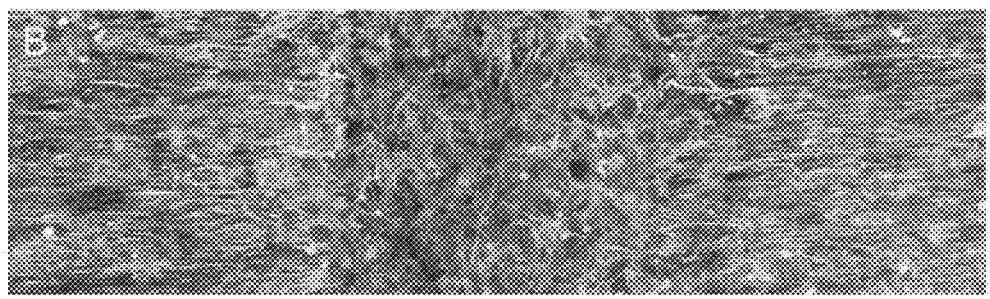
Figure 5C:
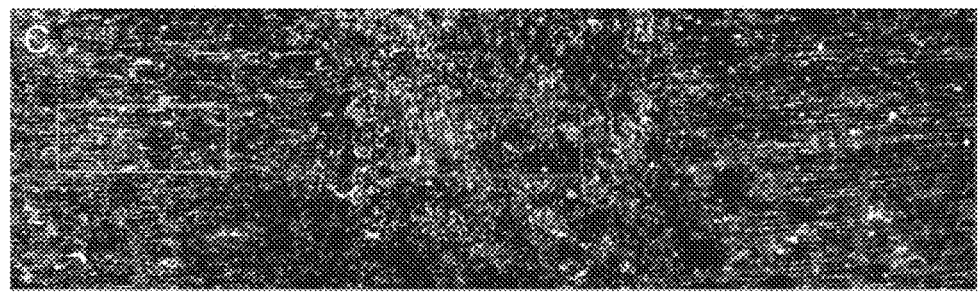
Figure 5D:
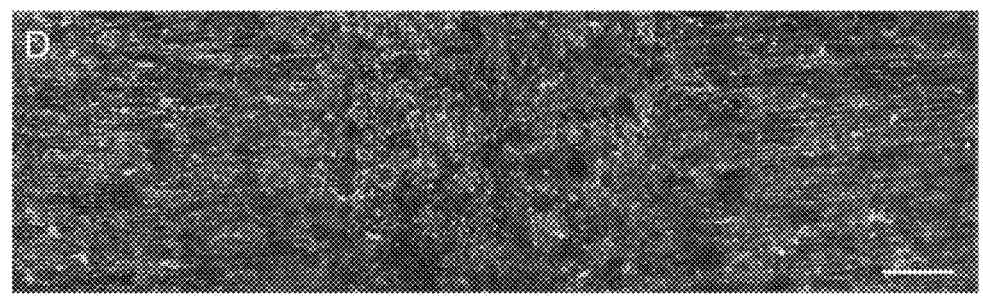
Figure 5E:
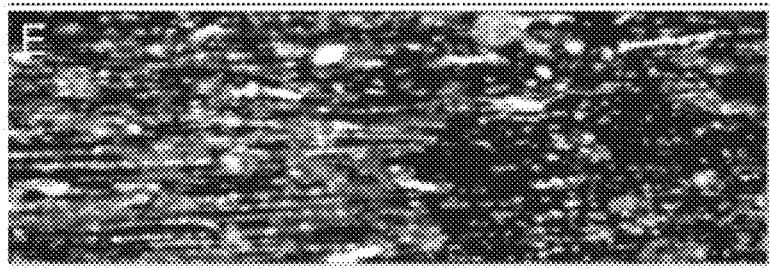
Figure 5F:
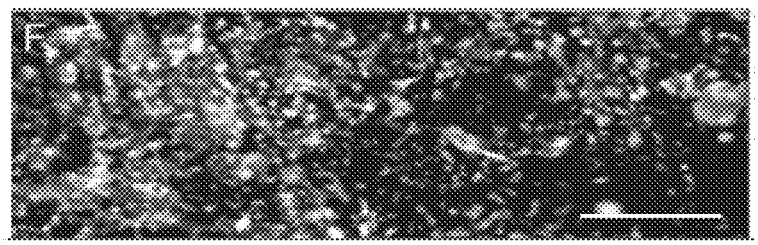
Figure 5G:
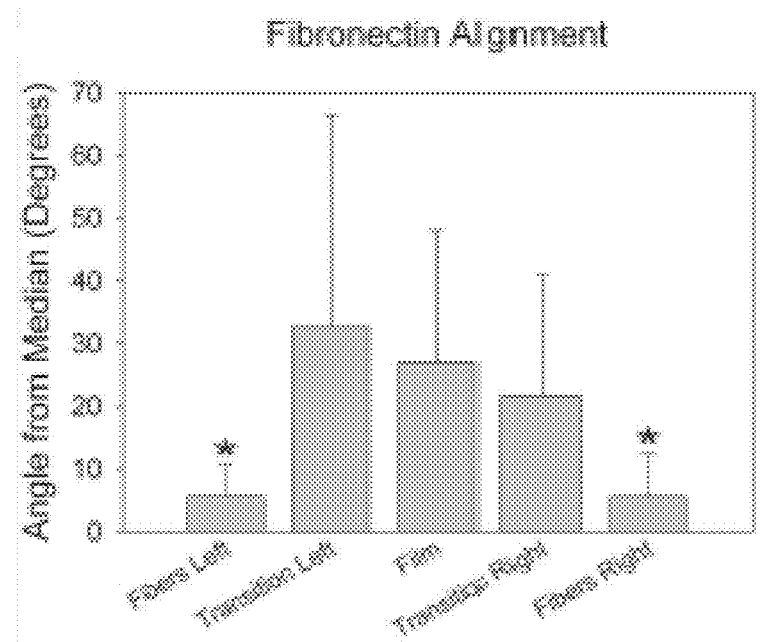

Previously, it has been shown that astrocytes cultured on aligned fibers have an aligned cytoskeleton, while the cytoskeletons of astrocytes cultured on PLLA films have no preferential orientation (Mongin et al., 2011). Similarly, others demonstrated aligned presentation of fibronectin produced by astrocytes cultured on adsorbed laminin patterns (Meng et al., 2012). Here, it was desired to examine the ability of aligned, PLLA fibers to orient the presentation of ECM molecules produced by astrocytes and to examine the orientation of ECM within the isotropic film region devoid of fibers. CSPGs (FIG. 4) and fibronectin (FIG. 5) were imaged to show their overall orientation on fibers and within the isotropic film region. Fluorescent PLLA fibers (FIG. 4A) and astrocytes (FIG. 4B) were imaged to again demonstrate the changes in astrocyte morphology when on the fibers compared to in the isotropic film regions. CSPGs were then imaged (FIG. 4C), and the composite image shows the expression of CSPGs compared to astrocyte location on the AFFT boundary scaffolds (FIG. 4D). CSPG expression was somewhat sparse throughout the AFFT boundary scaffolds (FIG. 4C), with limited expression from astrocytes located at any position. High magnification images were used to show the orientation of the disposition of CSPGs at different distances into and before the AFFT boundary. These data showed that astrocytes on the fibers presented CSPGs in a significantly more aligned manner (FIGS. 4E,G) than astrocytes located anywhere in the isotropic film region (FIGS. 4F,G). Alignment of the fibronectin produced by astrocytes was then determined. Fluorescent PLLA fibers (FIG. 5A) and astrocytes (FIG. 5B) were again imaged to show the presence of astrocytes on the AFFT boundary scaffolds. Astrocyte disposition of fibronectin was imaged (FIG. 5C), and the composite image shows the expression of fibronectin compared to astrocyte location on the AFFT boundary scaffolds (FIG. 5D). Fibronectin was highly expressed by astrocytes at all locations on the AFFT boundary scaffolds (FIG. 5C). High magnification images were used to show the orientation of fibronectin at different distances into and before the AFFT boundary. These data showed that astrocytes on the fibers presented fibronectin in a significantly more aligned manner (FIGS. 5E,G) than astrocytes located anywhere in the isotropic film regions (FIGS. 5F,G). These results demonstrate that astrocyte alignment affects the alignment of the disposition of astrocyte associated CSPGs and fibronectin.

Example 4: Neurite Outgrowth on Astrocyte Seeded AFFT Boundary Scaffolds

Figure 6A:
FIGS. 6A-I show that directed neurite growth is disrupted by the anisotropic-to-isotropic transition.
Figure 6B:
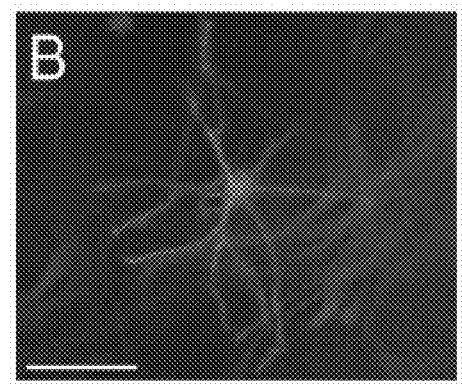
Figure 6C:
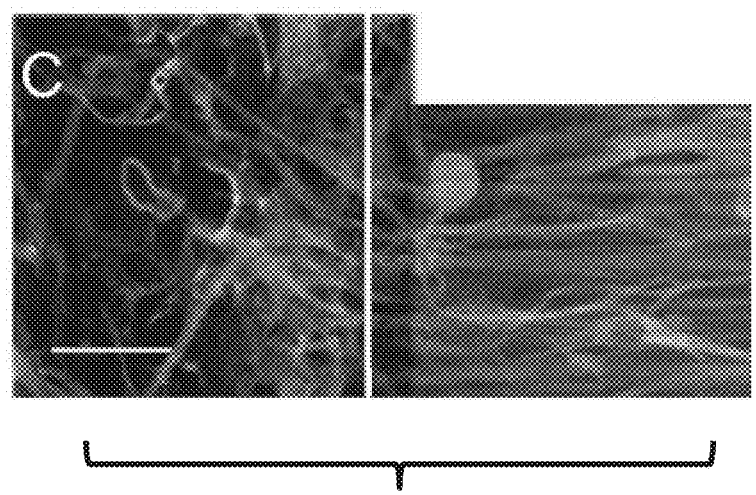
Figure 6D:
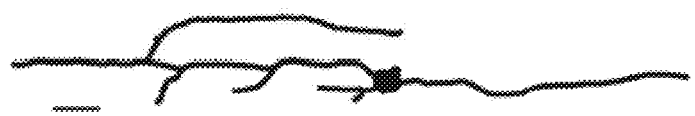
Figure 6E:
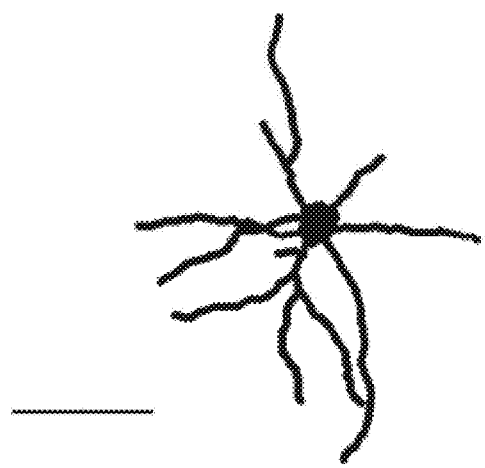
Figure 6F:
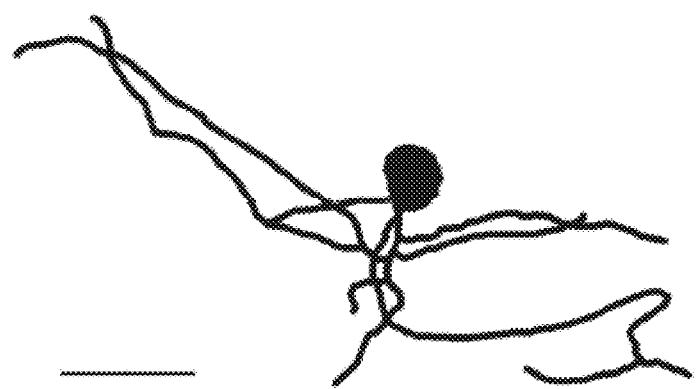
Figure 6G:
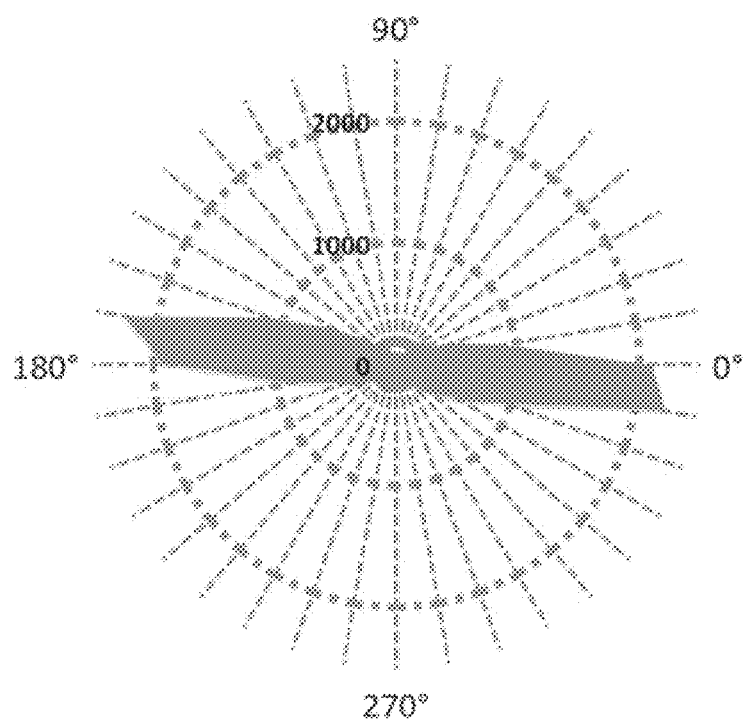
Figure 6H:
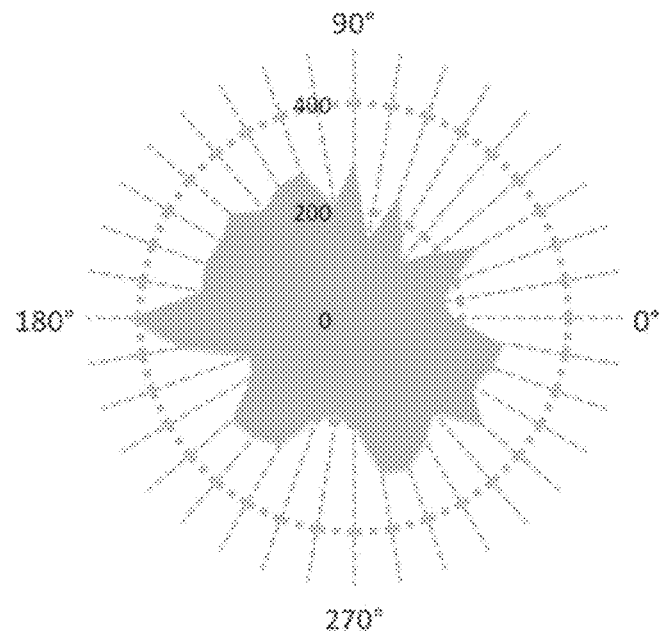
Figure 6I:
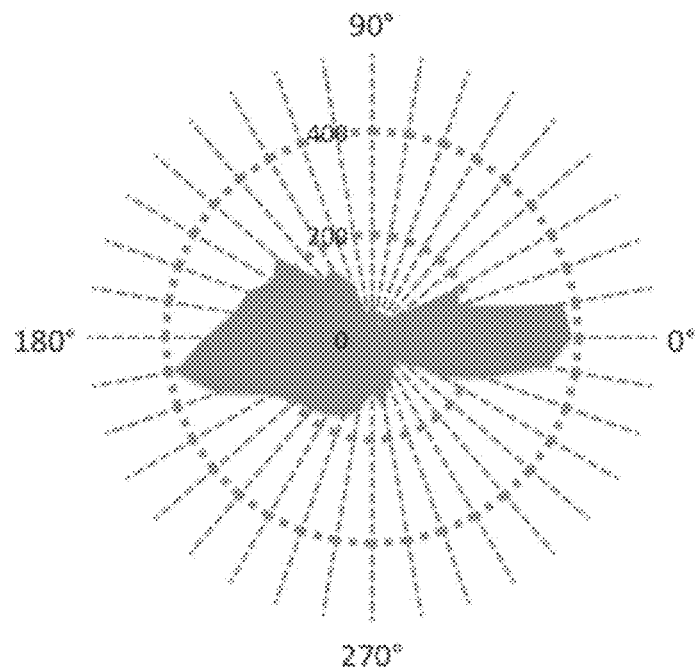
Figure 7A:
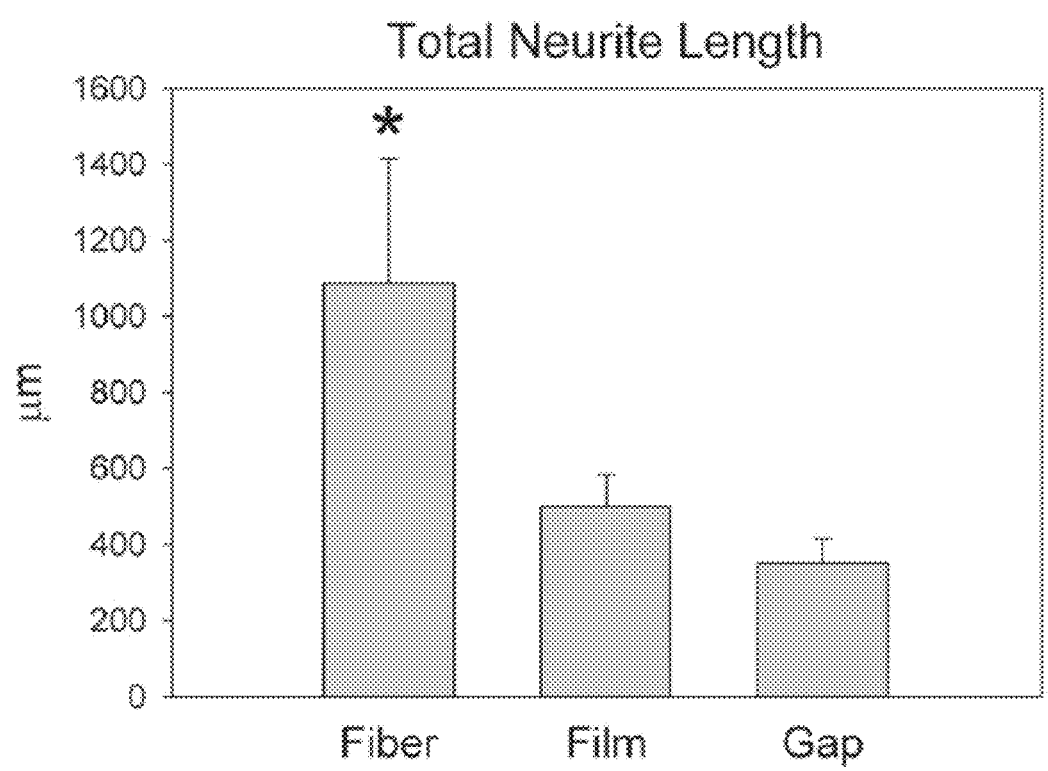
FIGS. 7A-B show a quantitative comparison of neurite outgrowth on aligned PLLA fibers, PLLA films, and PLLA fiber/AFFT.
Figure 7B:
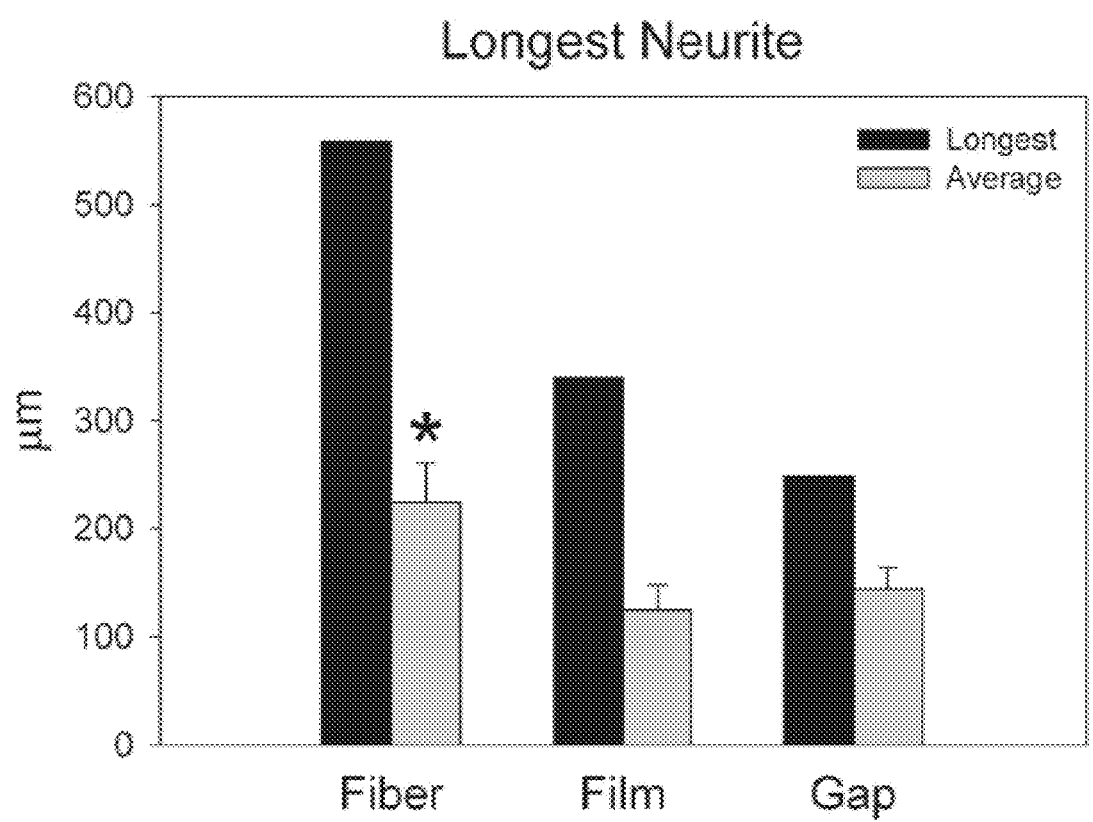

Previously, other studies have demonstrated that neurons cultured on aligned astrocytes extend oriented neurites that grow longer than neurons cultured on astrocytes grown on substrates lacking alignment (Meng et al., 2012; Chow et al., 2007; Biran et al., 2003). The AFFT boundary scaffold was designed to expand upon these findings and reveal how neurons interact with astrocytes at an anisotropic-to-isotropic transition. First, neurons were cultured on astrocytes that had been seeded on aligned PLLA fibers (FIGS. 6A,D) and PLLA films (FIGS. 6B,E) to ensure that astrocytes on PLLA fibers oriented neurite outgrowth compared to astrocytes on PLLA films. Polar histograms were created from the neuron traces, and the histograms demonstrate that neurites on astrocytes and aligned PLLA fibers are oriented in the direction of the fibers (FIG. 6G), while neurites originating from neurons cultured on astrocytes and PLLA films have no preferential alignment (FIG. 6H). Neurons were then cultured on astrocytes cultured on AFFT boundary scaffolds (FIGS. 6C,F), and the neurites extending from these neurons were aligned while on the PLLA fibers (FIG. 6I, the right side of the histogram). However, when neurites extended into the isotropic film region, they began to lose this preferential alignment and their directed growth (FIG. 6I, the left side of the histogram). Total neurite length and the length of the longest neurite were then analyzed for the three groups. Neurites extended significantly longer (1086±329 μm) when cultured on astrocytes and aligned fibers compared to both the film control (500±84 μm) and near the AFFT boundaries (352±65 μm) (FIG. 7A). The length of the average longest neurite of each neuron was then analyzed, and neurons on aligned fibers had an average longest neurite of 224±37 μm and an overall longest neurite of 558 μm. The average longest neurite was significantly longer on fibers compared to the films, whose neurons had an average longest neurite of 125±23 µm and an overall longest neurite of 339 µm, and AFFT boundary scaffolds, whose neurons had an average longest neurite of 145±19 µm and an overall longest neurite of 249 µm (FIG. 7B).

Figures 8A, 8B, 8C, 8D, 8E, 8F:
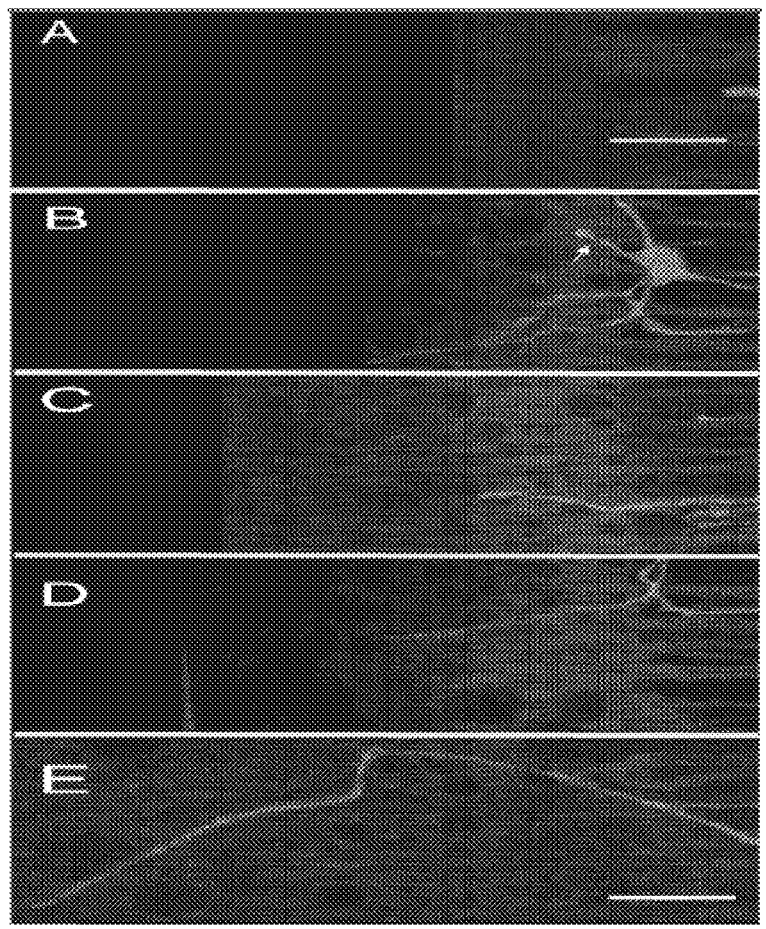
FIGS. 8A-F show that neurite growth is disrupted by the fiber-free region of the fiber/AFFT scaffolds.

Finally, neurite growth extending into the isotropic film region was analyzed to determine how the AFFT boundary affected neurite outgrowth. Once neurites reached the AFFT boundary, 25% of the neurites stopped and didn't enter the isotropic film region (FIGS. 8A,F). The majority of neurites extended less than 100 µm once they reached the AFFT boundary, with 39% growing between 0-50 µm (FIGS. 8B,F) and 21% growing between 50-100 µm into the isotropic film region (FIGS. 8C,F). Some neurites did extend greater than 100 µm into the isotropic film region, with 15% growing over 100 µm once they entered the isotropic film region (FIGS. 8D-F). These data demonstrate the ability of the AFFT boundaries to affect neurite outgrowth. In some situations, the anisotropic-to-isotropic transition stopped neurite extension all together or altered neurite extension and alignment once the neurites extended from the fibers into the isotropic film region.

The ability to study cellular responses to anisotropic-to-isotropic fiber/film transitions make the AFFT boundary biomaterial scaffolds provided by the present invention a unique platform for modeling injury sites in vitro. The ability of the biomaterial to recapitulate the lack of topographical guidance observed following SCI, where extending or regenerating neurites encounter first oriented astrocytes in injury free domains and subsequently unorganized astrocytes at the lesion edge, is demonstrated. Astrocytes cultured in the isotropic film regions did not display the alignment observed by astrocytes cultured on oriented PLLA fibers. The differences in astrocyte alignment were also translated in the fibronectin and CSPGs presented by these astrocytes. Neurons cultured onto the astrocytes adopted either oriented neurite outgrowth (on aligned astrocytes) or showed no preferential growth in any axis (disorganized astrocytes). The AFFT boundary restricted the growth of the majority of neurites that encountered this boundary. The scaffolds provided by the devices of the present invention are useful to validate the ability of pharmacological treatments to spur regeneration in non-topographical domains.

Discussion

The present invention demonstrates the utility of nebulized solvent-patterned electrospun microfiber scaffolds as in vitro central nervous system injury models. Nebulized chloroform was able to pattern microfiber scaffolds and not alter fiber orientation, diameter, or density, while creating a gradually sloping AFFT boundary. Cultured astrocytes showed distinct morphological differences when growing in the isotropic film region of the AFFT boundary scaffolds compared to on aligned fibers, and the differences in orientation were conveyed to both fibronectin and CSPGs produced by astrocytes. Neurite outgrowth was affected by the transitions from aligned astrocytes on fibers to unorganized astrocytes within the isotropic PLLA film domains. Neurites extending from the fibers and into the isotropic film region were affected by this change in cellular and substrate topography, and their orientation became less aligned while their growth was either stopped or slowed by the substrate transition. Overall, these results validate the use of this new biomaterial model for studying cellular responses to isotropic-to-anisotropic transitions.

The nebulized solvent patterning method utilized by the present invention is a robust method of creating transitional topographies in polymer based fiber scaffolds. The ease of creating rectangular isotropic film regions in the PLLA fibers (FIGS. 1,2) and the ability to create other shapes based on stencil patterns (FIG. 11) makes this new biomaterial platform an attractive method to further study cellular transitions in vitro. The formation of isotropic film regions in the PLLA fiber scaffolds had no discernable effects on fiber orientation, density, or diameter (FIG. 2). This is important for maintaining consistent fiber physical properties throughout the PLLA fiber scaffold. While other studies have analyzed cellular responses to changes in fiber alignment (Mongin et al., 2011), fiber diameter (Cheriyan et al., 2014), and fiber density (Xie et al., 2014), the present invention is unique due to the ability of the scaffold to study cellular responses to topological transitions. The AFFT boundary scaffold is a new example of a biomaterial that can be used as a platform to analyze cellular responses to topographical transitions. Developing biomaterial tools to help assess the ability of pharmacological agents to spur neurite outgrowth in isotropic domains may provide important validation prior to in vivo testing.

The AFFT boundary scaffolds presented herein allow for the in vitro evaluation of cellular responses to isotopic-to-anisotropic topographical transitions. These scaffolds are valuable for in vitro assessment of many injury paradigms (i.e. muscle injuries, tendon injuries, etc.). Following spinal cord injury, astrocytes at the lesion edge become unorganized and deviate from their typical alignment seen in the healthy spinal cord (Silver and Miller, 2004). Therefore, the astrocytes cultured on aligned fibers represent those aligned tracts, while astrocytes in the isotropic film regions represent the disorganized astrocytes seen in the lesion site. Astrocytes cultured on microfibers clearly aligned in the direction of fiber orientation, but when astrocytes were growing in the isotropic film regions they showed no preferential alignment (FIG. 3). The transition from aligned to non-oriented was abrupt, and astrocytes did not demonstrate preferential alignment even 50 µm into the isotropic film regions (FIG. 3). High magnification images revealed changes in the morphologies of individual astrocytes (FIG. 10). Astrocytes on the fibers projected oriented processes along the fiber direction, while astrocytes growing in the isotropic film regions produced processes that grew non-preferentially (FIG. 10). These results clearly demonstrate the differences between astrocyte growth on the two different areas of the substrate, and the astrocyte alignment also affected the alignment of ECM disposition produced by the astrocytes.

Neurite regeneration following central nervous system (CNS) injury is known to be affected by several ECM molecules produced by astrocytes. CSPGs inhibit neurite outgrowth following nervous system injury, and astrocytes are known to increase their production of CSPGs after CNS injury (Silver and Miller, 2004). Therefore, CSPG orientation was analyzed to understand how the different topographies affected astrocyte CSPG deposition. CSPGs produced and presented by astrocytes on the fibers were oriented in the direction of astrocyte and fiber alignment, but no alignment was seen from CSPGs presented by astrocytes growing in the isotropic film regions (FIG. 4). The high magnification images clearly depict this phenomenon, and they also demonstrate that CSPGs display a punctate expression pattern when produced by astrocytes growing on either the isotropic film regions or aligned topographies (FIG. 4). Meng et al. have demonstrated similar findings when comparing oriented and non-oriented astrocytes, where their expression of CSPGs is punctate for both morphologies of astrocytes (Meng et al., 2012). However, Meng et al. did not see oriented CSPG presentation by aligned astrocytes, which may be due to the differences by which the biomaterials induced astrocyte alignment (Meng et al. used laminin patterning of glass coverslips to impart cellular alignment). This may be due to differences in the size of the laminin patterns (15 µm) relative to the fiber diameter (3 µm), or the curvature effects of the fibers compared to the lack of curvature conveyed by the adsorbed laminin.

Fibronectin is an ECM molecule critical for axon regeneration in the white matter of adult rats (Tom et al., 2004). The alignment of fibronectin presented by astrocytes was analyzed, and it was again shown that fibronectin from aligned astrocytes is oriented in the direction of astrocytes and fiber alignment. However, fibronectin shows no preferential alignment when produced by astrocytes growing in the isotropic film regions (FIG. 5). There is a substantial amount of fibronectin produced by the astrocytes on both the aligned fibers and within the gaps, and the high magnification images clearly depict the alignment of this ECM molecule (FIG. 5). These results coincide with those demonstrated by Meng et al. on laminin-patterned substrates, where fibronectin produced by aligned astrocytes adopted the orientation of the astrocytes themselves (Meng et al., 2012).

The biomaterial platform of the present invention is able to recreate an important aspect of the CNS injury environment: oriented CNS astrocytes interfacing with disorganized astrocytes. While other in vitro platforms have focused on studying how neurons are affected by CSPG and laminin gradients (Wanner et al., 2013), chemically activated astrocytes (Yu et al., 2012), mechanically stretched co-cultures of astrocytes and fibroblasts (Wanner et al., 2008), or mixed glial cell cultures (Achyuta et al., 2010), this biomaterial platform was designed to specifically study how neurite extension was affected by astrocyte morphological transitions imparted by the AFFT boundary's topography. It has been shown that astrocytes cultured on aligned substrates have altered functions that mostly appear to be supportive of neuron survival and growth when compared to astrocytes cultured on topography free substrates (Zuidema. et al., 2014; Meng et al., 2012; Chow et al., 2007; Biran et al., 2003); Lau et al., 2014; Puschmann et al., 2013; Mattotti et al., 2012). In order to evaluate these effects in the AFFT boundary scaffolds of the present invention, overall neurite extension was first compared between neurons cultured on aligned PLLA fibers, films, or AFFT boundary scaffolds. The orientation of neurite outgrowth was evaluated to determine how the different substrates affected neurite growth. In agreement with several other studies (Meng et al., 2012; Chow et al., 2007; Biran et al., 2003), it was found that neurites extended parallel to astrocytes when cultured on oriented astrocytes (FIG. 6). Also, neurons cultured on the disorganized astrocytes grown on films demonstrated no preferential neurite extension (FIG. 6). Neurite alignment was then evaluated using the AFFT boundary model. Neurites were evaluated that extended from the aligned fibers and into the isotropic film region. Those that were growing on the fibers maintained highly oriented outgrowth parallel to astrocyte and fiber alignment (FIG. 6). However, once the neurites reached the AFFT boundary and crossed into the isotropic film region, they lost their growth guidance and began deviating from their aligned growth (FIG. 6). The loss in neurite guidance is likely due to the disorganization of the astrocytes within the fiber-free isotropic film region. Previously, Meng et al. provided evidence that neurites follow aligned fibronectin produced by oriented astrocytes Meng et al., 2012). The data provided herein coincides with these results, which provide an explanation for why neurites lose their guidance once they begin growing on the disorganized astrocytes. However, CSPGs are also presented in an aligned manner on the astrocytes cultured on PLLA fibers, and they too lose their alignment when the astrocytes are unaligned. The inhibitory nature of these molecules suggests that when they are aligned, neurites may be directed between several lanes of these molecules. This may act to guide the neurites in a directed manner. This ability to direct neurite growth through inhibition has been demonstrated using an in vitro CSPG strip assay (Vahidi et al., 2008), where neurites extended in between two separate lanes of CSPGs. Once the CSPGs are disorganized in the gap, the inhibition is no longer acting to direct the neurites down a parallel lane, but is completely redirecting their growth down another avenue of growth. These results, taken with the fibronectin results, suggest that the ECM molecules presented by astrocytes have an important effect on the orientation of growth of co-cultured neurons.

Neurons were also evaluated to determine their total neurite length and longest neurites. It was found that neurons cultured on aligned fibers had significantly longer total neurite length and longer average longest neurites compared to the neurons grown on films or near the AFFT boundaries (FIG. 7). The longest neurite on any of the substrates was also observed on the aligned fiber substrate. The fact that there are no differences between extending neurites on films or cultured near the AFFT boundaries led to investigation of what was happening to neurites that extended towards and into the isotropic film regions. Previously, Hynds et al., 2001 and Tom et al. 2004 studied how neurites grew into cell free regions of adsorbed inhibitory CSPGs in vitro by measuring neurite stopping, stalling, turning, or crossing of the inhibitory area. The studies provided herein analyzed neurites that extended from the fibers into the isotropic film region in order to quantify the distance they traveled after encountering this topographical change. It was found that 25% of all the neurites extending towards the gap stopped growing once they reached this boundary, 39% extended between 0-50 µm into the isotropic film region, 21% extended 50-100 µm into the isotropic film region, and only 14% extended over 100 µm once they encountered the AFFT boundary (FIG. 8). These data suggest that the transition of astrocytes from oriented to disorganized not only causes neurites to lose directional guidance, but that this boundary also acts to restrict the growth of neurites. The gradual, nanometer change in scaffold height (FIG. 9) suggests that the changes in neurite growth are not due to the change in scaffold height, but are due to the change in the orientation of the astrocytes and the molecules that they present. The average longest neurite on the AFFT boundary scaffolds was 145 µm, and since only about 7% of the neurites growing in the isotropic film region grew longer than 145 µm, the majority of the longest neurites from each neuron are not neurites that are extending into the gap. Most of the longest neurites for these neurons are extending on the fibers and not encountering the AFFT boundary. Therefore, this growth restriction caused by the boundary between organized and disorganized astrocytes may account for the fact that there are no differences in neurite outgrowth seen between PLLA films and the AFFT boundary scaffolds.

The AFFT boundary scaffold of the present invention was developed as a biomaterial substrate to model anisotropic-to-isotropic transitions in vitro. Modeling the changes in astrocyte alignment following spinal cord injury was chosen due to the lack of in vitro models that are capable of modeling this aspect of the injury. One important aspect of any spinal cord injury model is the ability of the model to restrict neurite outgrowth. The results provided herein demonstrated this capability; 25% of the extending neurites stopped at the AFFT boundary, while 85% extended less than 100 µm once they entered the isotropic film region. This is not as inhibitory as some injury models, such as CSPG gradient models (Tom et al., 2004; Hynds and Snow, 2001), where less than 1% of extending neurites grow onto the deposited CSPGs unless a growth supportive ECM molecule (fibronectin or laminin) is present. However, this looks at a different aspect of the injury than other models. The CSPG gradients look solely at how neurite extension is affected by molecules adsorbed onto glass substrates. The model provided by the present invention looks at a different aspect of the injury, the change from oriented to disorganized astrocytes.

Astrocytes produce a variety of factors, and including them in the injury model allows for neurons to experience many different factors while extending neurites. Recently, a study by Weightman et al. developed an ex vivo spinal cord injury model designed to test the viability of biomaterial platforms before they are transplanted in vivo (Weightman et al., 2014). This ex vivo model utilizes spinal cord sections that are lesioned with a scalpel and then bridged with poly-lactic acid nanofibers. This model increases the number of biomaterials that can be tested on each animal; however, this ex vivo model does not possess the ease of use for an initial analysis that a cell culture model does. Also, these tissue sections are taken from only one animal, but cell culture studies can test cells from multiple animal sources in a single culture. While Weightman et al. developed a robust ex vivo model to test biomaterial platforms, aspects of the present invention aimed to develop a biomaterial that modeled the injury site. The model provided by aspects of the present invention presents a first step in testing therapeutic interventions that increase the growth capacity of neurons. Producing reactive astrocytes in the AFFT boundary system by including a molecular activator in the culture medium is contemplated by this invention. This would further inhibit neuronal extension in general, and increase restricted growth at the AFFT boundary. Regardless, the astrocytes cultured in this anisotropic-to-isotropic fiber/film transition boundary scaffold make the present invention a unique in vitro model of the organizational transitions of astrocytes encountered by neurons following SCI.

REFERENCES

[1] Anselme K, Davidson P, Popa A M, Giazzon M, Liley M, Ploux L. The interaction of cells and bacteria with surfaces structured at the nanometer scale. Acta Biomater 2010; 6:3824-46.

[2] Hoffman-Kim D, Mitchel J A, Bellamkonda R V. Topography, cell response, and nerve regeneration. Annu Rev Biomed Eng 2010; 12:203-31.

[3] Lim J Y, Donahue H J. Cell sensing and response to micro- and nanostructured surfaces produced by chemical and topographic patterning. Tissue Eng 2007; 13:1879-91.

[4] Turner A M, Dowell N, Turner S W, Kam L, Isaacson M, Turner J N, et al. Attachment of astroglial cells to microfabricated pillar arrays of different geometries. J Biomed Mater Res 2000; 51:430-41.

[5] Gomez N, Lu Y, Chen S, Schmidt C E. Immobilized nerve growth factor and microtopography have distinct effects on polarization versus axon elongation in hippocampal cells in culture. Biomaterials 2007; 28:271-84.

[6] Bechara S L, Judson A, Popat K C. Template synthesized poly(epsilon-caprolactone) nanowire surfaces for neural tissue engineering. Biomaterials 2010; 31:3492-501.

[7] Corey J M, Lin D Y, Mycek K B, Chen Q, Samuel S, Feldman E L, et al. Aligned electrospun nano-fibers specify the direction of dorsal root ganglia neurite growth. J Biomed Mater Res A 2007; 83:636-45.

[8] Wang H B, Mullins M E, Cregg J M, Hurtado A, Oudega M, Trombley M T, et al. Creation of highly aligned electrospun poly-L-lactic acid fibers for nerve regeneration applications. J Neural Eng 2009; 6:016001.

[9] Chew S Y, Mi R, Hoke A, Leong K W. The effect of the alignment of electrospun fibrous scaffolds on Schwann cell maturation. Biomaterials 2008; 29:653-61.

[10] Bellamkonda R V. Peripheral nerve regeneration: an opinion on channels, scaffolds and anisotropy. Biomaterials 2006; 27:3515-8.

[11] Silver J, Miller J H. Regeneration beyond the glial scar. Nat Rev Neurosci 2004; 5:146-56.

[12] Chew S Y, Mi R, Hoke A, Leong K W. Aligned protein-polymer composite fibers enhance nerve regeneration: a potential tissue-engineering platform. Adv Funct Mater 2007; 17:1288-96.

[13] Kim Y T, Haftel V K, Kumar S, Bellamkonda R V. The role of aligned polymer fiber-based constructs in the bridging of long peripheral nerve gaps. Biomaterials 2008; 19:3117-27.

[14] Gelain F, Panseri S, Antonini S, Cunha C, Donega M, Lowery J, et al. Transplantation of nanostructured composite scaffolds results in the regeneration of chronically injured spinal cords. ACS Nano 2011; 5:227-236.

[15] Hurtado A, Cregg J M, Wang H B, Wendell D F, Oudega M, Gilbert R J, et al. Robust CNS regeneration after complete spinal cord transection using aligned poly-L-lactic acid microfibers. Biomaterials 2011; 32:6068-6079.

[16] Liu T, Houle J D, Xu J, Chan B P, Chew S Y. Nanofibrous collagen nerve conduits for spinal cord repair. Tissue Eng Part A 2012; 18:1057-1066.

[17] Koppes A N, Zaccor N W, Rivet C J, Williams L A, Piselli J M, Gilbert R J, et al. Neurite outgrowth on electrospun PLLA fibers is enhanced by exogenous electrical stimulation. J. Neural Eng. 2014; 11:046002.

[18] Wanner I B, Anderson M A, Song B, Levine J, Fernandez A, Gray-Thompson Z, et al. Glial scar borders are formed by newly proliferated, elongated astrocytes that interact to corral inflammatory and fibrotic cells via STAT3-dependent mechanisms after spinal cord injury. J. Neurosci 2013; 33:12870-86.

[19] Tom V J, Steinmetz M P, Miller J H, Doller C M, Silver J. Studies on the development and behavior of the dystrophic growth cone, the hallmark of regenerative failure, in an in vitro model of the glial scar and after spinal cord injury. J Neurosci 2004; 24:6531-9.

[20] Sharma K, Slezer M E, Li S. Scar-mediated inhibition and CSPG receptors in the CNS. Exp Neurol 2012; 237:370-8.

[21] Pernet V and Schwab M E. The role of Nogo-A in axonal plasticity, regrowth, and repair. Cell Tissue Res 2012; 349:97-104.

[22] Cheng H, Cao Y, Olson L. Spinal cord repair in adult paraplegic rats: partial restoration of hind limb function. Science 1996; 273:510-3.
[23] Cheriyan T, Ryan D J, Weinreb J H, Cheriyan J, Paul J C, Lafage V, et al. Spinal cord injury models: a review. Spinal Cord 2014; In Press.
[24] Wang H B, Mullins M E, Cregg J M, McCarthy C W, Gilbert R J. Varying the diameter of aligned electrospun fibers alters neurite outgrowth and Schwann cell migration. Acta Biomater 2010; 6:2970-8.
[25] Mongin A A, Hyzinski-Garcia M C, Vincent M Y, Keller Jr R W. A simple method for measuring intracellular activities of glutamine synthetase and glutaminase in glial cells. Am J Physiol Cell Physiol 2011; 301:C814-22.
[26] Zuidema J M, Hyzinski-Garcia M C, Van Vlasselaer K, Zaccor N W, Plopper G E, Mongin A A, et al. Enhanced GLT-1 mediated glutamate uptake and migration of primary astrocytes directed by fibronectin-coated electrospun poly-L-lactic acid fibers. Biomaterials 2014; 35:1439-49.
[27] Koppes A N, Seggio A M, Thompson D M. Neurite outgrowth is significantly increased by the simultaneous presentation of Schwann cells and moderate exogenous electric fields. J Neural Eng 2011; 8:046023.
[28] Christopherson G T, Song H, Mao H Q. The influence of fiber diameter of electrospun substrates on neural stem cell differentiation and proliferation. Biomaterials 2009; 30:556-64.
[29] Meng F, Hlady V, Tresco P A. Inducing alignment in astrocyte tissue constructs by surface ligands patterned on biomaterials. Biomaterials 2012; 33:1323-35.
[30] Chow W N, Simpson D G, Bigbee J W, Colello R J. Evaluating neuronal and glial growth on electrospun polarized matrices: bridging the imp in percussive spinal cord injuries. Neuron Glia Biol. 2007; 3:119-26.
[31] Biran R, Noble M D, Tresco P A. Directed nerve outgrowth is enhanced by engineered glial substrates. Exp. Neurol. 2003; 184:141-52.
[32] Xie J, Liu W, MacEwan M R, Bridgman P C, and Xia Y. Neurite Outgrowth on Electrospun Nanofibers with Uniaxial Alignment: The Effects of Fiber Density, Surface Coating, and Supporting Substrate. *ACS nano* 2014; 8:1878-85.
[33] Tom V J, Doller C M, Malouf A T, Silver J. Astrocyte-associated fibronectin is critical for axonal regeneration in adult white matter. J. Neurosci. 2004; 24:9282-90.
[34] Yu P, Wang H, Katagiri Y, Geller H M. An in vitro model of reactive astrogliosis and its effect on neuronal growth. Methods Mol. Biol. 2012; 814:327-40.
[35] Wanner I B, Deik A, Torres M, Rosendahl A, Neary J T, Lemmon V P, et al. A new in vitro model of the glial scar inhibits axon growth. Glia. 2008; 56:1691-709
[36] Achyuta A K H, Polikov V S, White A J, Lewis H G P, Murthy S K. Biocompatibility assessment of insulating silicone polymer coatings using an in vitro glial scar assay. Macromol. Biosci. 2010; 10:872-80.
[37] Vahidi B, Park J W, Kim H J, Jeon N L. Microfluidic-based strip assay for testing the effects of various surface-bound inhibitors in spinal cord injury. J. Neurosci. Methods. 2008; 170:188-96.
[38] Hynds D L, Snow D M. Fibronectin and laminin elicit differential behaviors from SH-SY5Y growth cones contacting inhibitory chondroitin sulfate proteoglycans. J. Neurosci. Res. 2001; 66:630-42.
[39] Weightman A P, Pickard M R, Yang Y, Chari D M. An in vitro spinal cord injury model to screen neuroregenerative materials. Biomaterials. 2014; 35:3756-65.
[40] Lau C L, Kovacevic M, Tingleff T S, Forsythe J S, Cate H S, Merlo D, Cederfur C, et al. 3D Electrospun scaffolds promote a cytotrophic phenotype of cultured primary astrocytes. J. of neurochem. 2014; In Press
[41] Puschmann T B, Zand C, De Pablo Y, Kirchhoff F, Pekna M, Liu J, et al. Bioactive 3D cell culture system minimizes cellular stress and maintains the in vivo-like morphological complexity of astroglial cells. Glia. 2013; 61:432-40.
[42] Mattotti M, Alvarez Z, Ortega J A, Planell J A, Engel F, Alcantara S. Inducing functional radial glia-like progenitors from cortical astrocyte cultures using micropatterned PMMA. Biomaterials. 2012, 33:1759-70.
[43] R. Rezakhaniha, A. Agianniotis, J. T. Schrauwen, A. Griffa, D. Sage, C. V. Bouten et al. Experimental investigation of collagen waviness and orientation in the arterial adventitia using confocal laser scanning microscopy. Biomech Model Mechanobiol. 2012; 11:461-473 diamond pattern (A), a circle (B), a triangle (C), and a square (D) Scale bar in A=1 mm and can be applied to B, C, and D.

We claim:

1. A cell culture apparatus for modeling isotropic-to-anisotropic cellular transitions, comprising:
   a substrate comprising an isotropic film surface with one or more regions of aligned fibers dispersed thereon, wherein the one or more regions of aligned fibers and the isotropic film surface provide a topographic-to-non-topographic transitional boundary therebetween.

2. The apparatus of claim 1, wherein the one or more fibers are electrospun fibers.

3. The apparatus of claim 1, wherein the one or more fibers comprise poly-L-lactic acid.

4. The apparatus of claim 1, wherein the isotropic film surface comprises poly-L-lactic acid.

5. The apparatus of claim 1, wherein the topographic-to-non-topographic transitional boundary is formed by dissolving a portion of the aligned fibers.

6. A method of fabrication of a cell culture apparatus comprising fiber scaffolds for modeling isotropic-to-anisotropic cellular transitions, comprising:
   depositing a collection film onto a substrate;
   depositing fibers onto the collection film to form fiber scaffolds; and dissolving a portion of the deposited fibers to yield one or more regions of an isotropic film surface that transition from the fiber scaffolds to form an anisotropic-to-isotropic fiber/film boundary.

7. The method of claim 6, wherein the deposited fibers are aligned.

8. The method of claim 6, wherein the deposited fibers are dissolved with chloroform.

9. The method of claim 6, wherein the collection film comprises poly-L-lactic acid.

10. The method of claim 6, wherein the fibers comprise poly-L-lactic acid.

11. A method of modeling in vivo cellular response to isotropic-to-anisotropic topographic transitions in an in vitro model for tissue injury, comprising:
    providing an apparatus of claim 1;
    seeding one or more cells onto the substrate;
    allowing the one or more cells to adhere to the one or more regions of aligned fibers; and
    allowing the one or more cells to grow, whereby cell growth within the transitional boundary between the aligned fibers and the isotropic film surface models in vivo isotropic-to-anisotropic topographic transitions of injured tissue.

12. The method of claim 11, wherein the one or more cells are derived from neural tissue.

13. A kit for examining cellular response to isotropic-to-anisotropic transitions, comprising:
   an apparatus of claim 1; and
   one or more reagent.

* * * * *